(12) United States Patent
Sommer et al.

(10) Patent No.: US 9,901,732 B2
(45) Date of Patent: Feb. 27, 2018

(54) MEDICAL ELECTRICAL LEAD

(71) Applicant: Medtronic, Inc., Minneapolis, MN (US)

(72) Inventors: John L Sommer, Coon Rapids, MN (US); William J Clemens, Fridley, MN (US); Linda L Franke, Fridley, MN (US)

(73) Assignee: Medtronic, Inc., Minneapolis, MN (US)

( * ) Notice: Subject to any disclaimer, the term of this patent is extended or adjusted under 35 U.S.C. 154(b) by 120 days.

(21) Appl. No.: 14/523,137

(22) Filed: Oct. 24, 2014

(65) Prior Publication Data

US 2016/0114152 A1 Apr. 28, 2016

(51) Int. Cl.
*A61N 1/05* (2006.01)
*A61N 1/362* (2006.01)

(52) U.S. Cl.
CPC ............ *A61N 1/056* (2013.01); *A61N 1/0563* (2013.01); *A61N 1/3622* (2013.01); *A61N 2001/0585* (2013.01)

(58) Field of Classification Search
CPC ...... A61N 1/05; A61N 1/0504; A61N 1/0507; A61N 1/0509; A61N 1/0512; A61N 1/0514; A61N 1/0517; A61N 1/0519; A61N 1/0521; A61N 1/0524; A61N 1/0526; A61N 1/0551; A61N 1/056; A61N 1/0563; A61N 1/0565; A61N 1/0587; A61N 1/0592
See application file for complete search history.

(56) References Cited

U.S. PATENT DOCUMENTS

| | | |
|---|---|---|
| 4,428,378 A | 1/1984 | Anderson et al. |
| 5,052,388 A | 10/1991 | Sivula et al. |
| 5,127,403 A | 7/1992 | Brownlee |
| 5,387,233 A | 2/1995 | Alferness et al. |
| 5,628,779 A | 5/1997 | Bornzin et al. |
| 5,683,445 A | 11/1997 | Swoyer |

(Continued)

FOREIGN PATENT DOCUMENTS

WO 2007097859 A1 8/2007

OTHER PUBLICATIONS (PCT/US2015/057118) PCT Notification of Transmittal of the International Search Report and the Written Opinion of the International Searching Authority, mailed Mar. 14, 2016, 12 pages.

(Continued)

*Primary Examiner* — Todd J Scherbel

(57) ABSTRACT

The present disclosure may comprise an improvement to the prior art leads as disclosed above. One embodiment is directed to an intravenous medical electrical lead that includes an elongated lead body. The elongated lead body comprises a length between proximal and distal ends with a longitudinal axis extending therebetween. The distal end of the lead body includes a plurality of electrodes forming first and second pairs of electrodes. The first pair of electrodes comprises one electrode electrically connected to another electrode circumferentially and diagonally spaced apart along the longitudinal axis. The second pair of electrodes comprising one electrode electrically connected to another electrode circumferentially and diagonally spaced apart along the longitudinal axis.

26 Claims, 14 Drawing Sheets

(56) References Cited

U.S. PATENT DOCUMENTS

| | | | |
|---|---|---|---|
| 5,800,465 | A | 9/1998 | Thompson et al. |
| 5,925,073 | A | 7/1999 | Chastain et al. |
| 5,991,668 | A | 11/1999 | Leinders et al. |
| 5,999,858 | A | 12/1999 | Sommer et al. |
| 6,021,354 | A | 2/2000 | Warman et al. |
| 6,129,750 | A | 10/2000 | Tockman et al. |
| 6,144,882 | A | 11/2000 | Sommer et al. |
| 6,278,894 | B1 | 8/2001 | Salo et al. |
| 6,321,123 | B1 | 11/2001 | Morris et al. |
| 6,418,348 | B1 | 7/2002 | Witte |
| 6,430,449 | B1 | 8/2002 | Hsu et al. |
| 6,757,970 | B1 | 7/2004 | Kuzma et al. |
| 6,978,178 | B2 | 12/2005 | Sommer et al. |
| 7,047,084 | B2 | 5/2006 | Erickson et al. |
| 7,313,444 | B2 | 12/2007 | Pianca et al. |
| 7,383,091 | B1 | 6/2008 | Chitre et al. |
| 7,532,939 | B2 | 5/2009 | Sommer et al. |
| 7,601,033 | B2 | 10/2009 | Ries et al. |
| 7,654,843 | B2 | 2/2010 | Olson et al. |
| 7,684,863 | B2 | 3/2010 | Parikh et al. |
| 7,860,580 | B2 | 12/2010 | Falk et al. |
| 7,881,806 | B2 | 2/2011 | Horrigan et al. |
| 7,974,705 | B2 | 7/2011 | Zdeblick et al. |
| 8,036,743 | B2 | 10/2011 | Savage et al. |
| 8,295,943 | B2 | 10/2012 | Eggen et al. |
| 8,437,866 | B2 | 5/2013 | Gebauer et al. |
| 8,498,721 | B2 | 7/2013 | Scheiner et al. |
| 8,755,909 | B2 | 6/2014 | Sommer et al. |
| 2002/0193834 | A1 | 12/2002 | Levine |
| 2003/0050681 | A1 | 3/2003 | Pianca et al. |
| 2003/0105501 | A1 | 6/2003 | Warman et al. |
| 2003/0195603 | A1 | 10/2003 | Scheiner et al. |
| 2003/0220676 | A1 | 11/2003 | Helland |
| 2005/0090870 | A1 | 4/2005 | Hine et al. |
| 2006/0253182 | A1* | 11/2006 | King ............ A61N 1/0551 607/117 |
| 2007/0249997 | A1 | 10/2007 | Goodson, IV et al. |
| 2008/0114230 | A1 | 5/2008 | Addis |
| 2009/0171381 | A1 | 7/2009 | Schmitz et al. |
| 2010/0268298 | A1 | 10/2010 | Moffitt et al. |
| 2011/0005069 | A1 | 1/2011 | Pianca |
| 2011/0238129 | A1 | 9/2011 | Moffitt et al. |
| 2012/0203316 | A1 | 8/2012 | Moffitt et al. |
| 2013/0131748 | A1 | 5/2013 | Stadler et al. |

OTHER PUBLICATIONS (PCT/US2015/057123) PCT Notification of Transmittal of the International Search Report and the Written Opinion of the International Searching Authority, mailed Jan. 28, 2016, 12 pages.

(PCT/US2015/057251) PCT Notification of Transmittal of the International Search Report and the Written Opinion of the International Searching Authority, mailed Feb. 4, 2016, 10 pages.

(PCT/US2015/057253) PCT Notification of Transmittal of the International Search Report and the Written Opinion of the International Searching Authority, mailed Feb. 9, 2016, 11 pages.

* cited by examiner

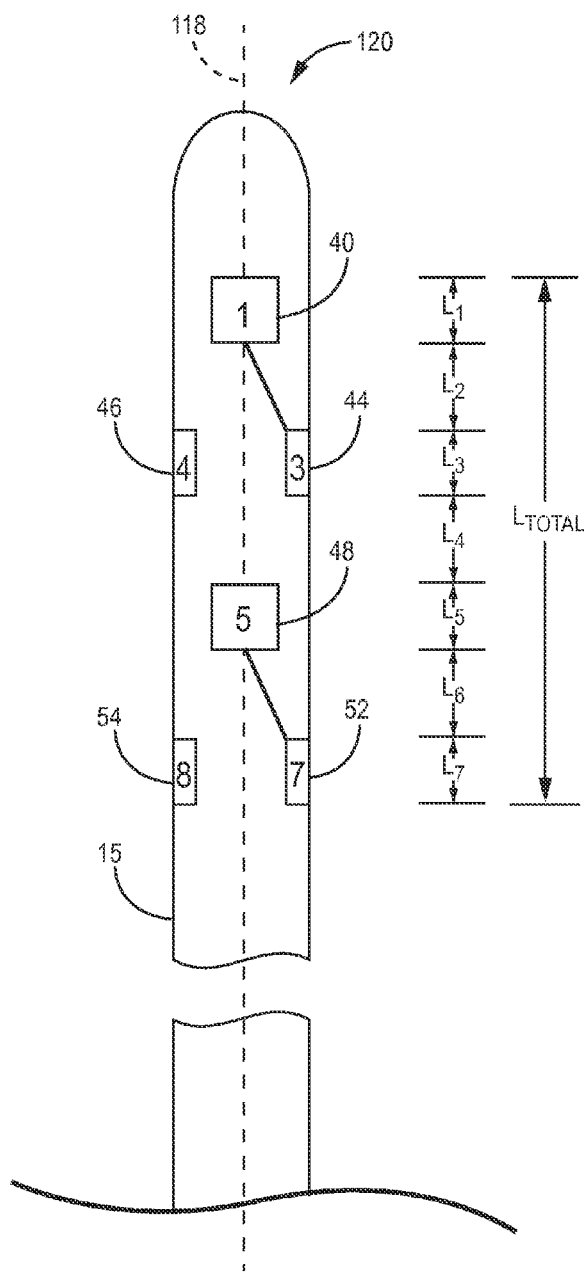
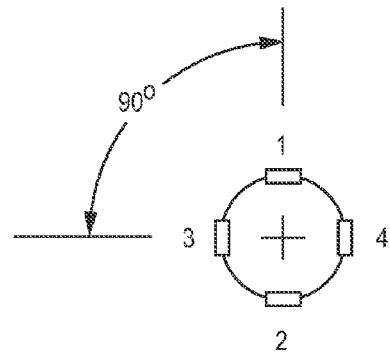
FIG. 4
FIG. 5

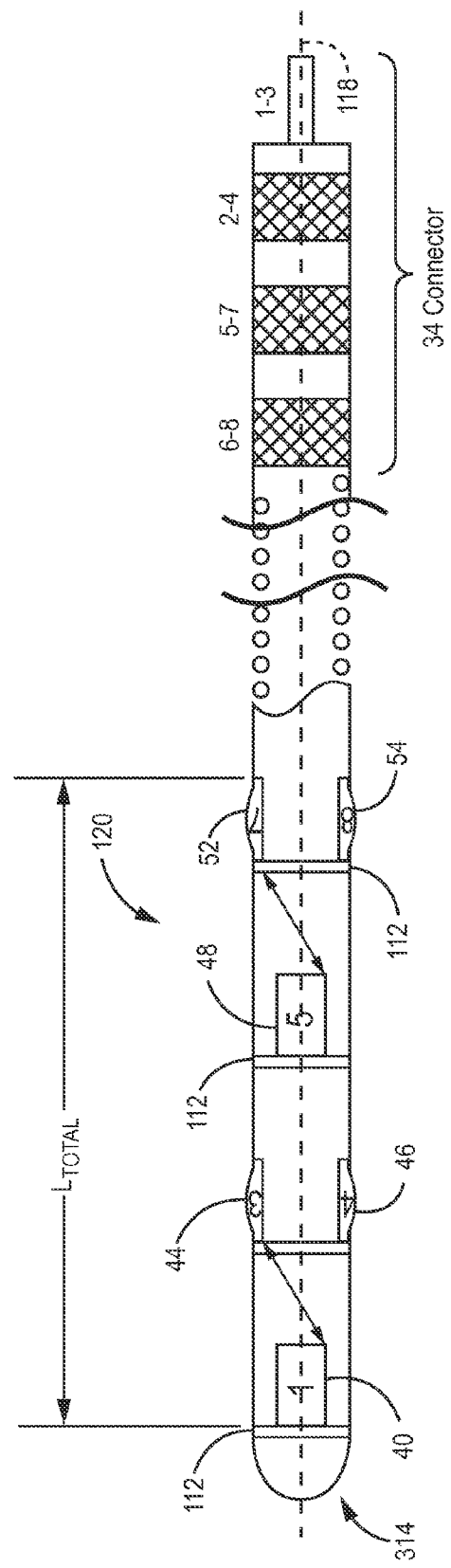
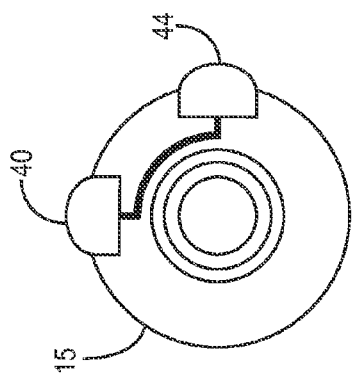
FIG. 9
FIG. 10

MEDICAL ELECTRICAL LEAD

TECHNICAL FIELD

The present disclosure pertains to medical electrical leads, and, more particularly, to implantable medical electrical leads that increase delivery of electrical stimuli options.

BACKGROUND

Implantable medical devices, for example cardiac pacemakers and defibrillators, often include elongate medical electrical leads having one or more electrodes to sense electrical activity and deliver therapeutic stimulation. With the advent of left ventricular pacing to alleviate heart failure, leads have been advanced into the coronary veins in order to position the electrodes of the leads at left ventricular pacing sites, typically located in proximity to the base of the left ventricle. Although a variety of left ventricular pacing leads, along with methods for implanting such leads, have been developed, there is still a need for a lead including features that facilitate delivery to, and fixation at, sites in the coronary vasculature.

Numerous types of medical electrical leads can be adapted for placement in coronary vasculature. Exemplary active fixation leads include U.S. Pat. No. 7,860,580, issued to Sommer, et al., U.S. Pat. No. 7,532,939, issued to Sommer, et al. and U.S. patent application Ser. No. 13/793,622, filed Mar. 11, 2013 by Sommer, et al., all of which are incorporated herein by reference in their entirety. Shaped leads can also be adaped for placement in the coronary vasculature. Exemplary shaped leads or catheters include U.S. Pat. No. 7,313,444, issued to Pianca et al., U.S. Pat. No. 5,387,233, issued to Alferness, et al., U.S. Pat. No. 5,925,073, issued to Chastain, et al., U.S. Pat. No. 6,430,449, issued to Hsu, et al., U.S. Pat. No. 6,129,750, issued to Tockman et al., U.S. Pat. No. 6,321,123 issued to Morris. Some implantable medical devices are configured to pace from multiple electrodes on the lead such as U.S. Pat. No. 8,036,743. However, ring electrodes spaced apart and aligned longitudinally provide limited electrical field gradients that may not achieve optimal stimulation locations for some patients. It is therefore desirable to develop a medical electrical lead that provides increased options for delivery of effective therapy.

SUMMARY OF THE DISCLOSURE

The present disclosure may comprise an improvement to the prior art leads as disclosed above. One embodiment is directed to an intravenous medical electrical lead that includes an elongated lead body. The elongated lead body comprises a length between proximal and distal ends with a longitudinal axis extending therebetween. The distal end of the lead body includes a plurality of electrodes forming first and second pairs of electrodes. The first pair of electrodes comprises one electrode electrically connected to another electrode circumferentially and diagonally spaced apart along the longitudinal axis. The second pair of electrodes comprising one electrode electrically connected to another electrode circumferentially and diagonally spaced apart along the longitudinal axis. In one or more other embodiments, each electrode is protrudes away from the outer circumference of the lead body.

In one more other embodiments, the lead can be shaped in numerous configurations (i.e straight, canted, S-Shaped or pigtailed). In still yet another embodiment, a helix for active fixation can be added to the lead. In another embodiment, the implantable medical device (e.g. ICD, IPG etc.) can be configured or programmed to tie two pairs of two electrodes together as anodes and the other two pairs of two electrodes can be cathodes.

For some patients, increased cardiac resynchronization response rate can be achieved through multiple diagonal electrodes on a lead coupled to an IS-4 connector module. In addition, greater tissue contact and reduced pacing thresholds is attained through the outer electrode surface, extending or protruding beyond the outer diameter of the lead body.

BRIEF DESCRIPTION OF THE DRAWINGS

The following drawings are illustrative of particular embodiments of the present disclosure and therefore do not limit the scope of the disclosure. The drawings are not to scale (unless so stated) and are intended for use in conjunction with the explanations in the following detailed description. Embodiments of the present disclosure will hereinafter be described in conjunction with the appended drawings, wherein like numerals denote like elements.

FIG. 4 is a schematic diagram of a front view of a set of electrodes positioned along a distal end of a lead.

FIG. 5 is a cross-sectional view of a set of electrodes positioned along a lead distal end.

FIG. 9 is a schematic diagram of a front view of a set of electrodes positioned along a lead distal end of a lead that is coupled to a connector module.

FIG. 10 is a cross-sectional top view of a set of electrodes positioned along a distal end of a lead.

DETAILED DESCRIPTION

The following detailed description is exemplary in nature and is not intended to limit the scope, applicability, or configuration of the disclosure in any way. Rather, the following description provides practical illustrations for implementing exemplary embodiments of the present invention. Constructions, materials, dimensions, and manufacturing processes suitable for making embodiments of the present are known to those of skill in the field of the invention.

Figure 1:
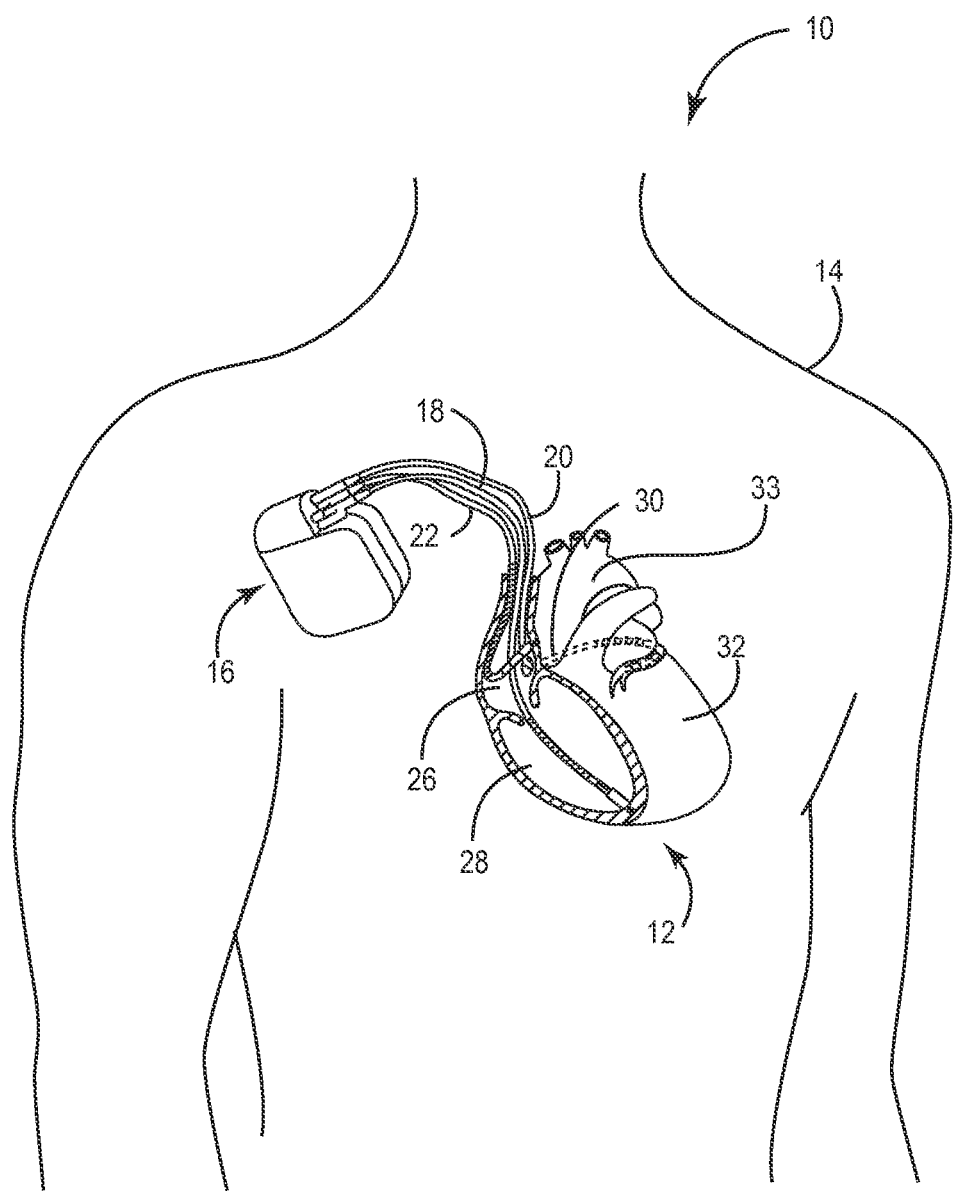
FIG. 1 is a diagram of an exemplary system including an exemplary implantable medical device (IMD).

FIGS. 1-3 generally depict and provide details as to the manner in which an exemplary therapy system operating in conjunction with a medical electrical lead while FIGS. 4-11 provide the details as to the present disclosure. FIG. 1 is a conceptual diagram illustrating an exemplary therapy system 10 that may be used to deliver pacing therapy to a patient 14. Patient 14 may, but not necessarily, be a human. The therapy system 10 may include an implantable medical device 16 (IMD), which may be coupled to leads 18, 20, 22. The IMD 16 may be, e.g., an implantable pacemaker, cardioverter, and/or defibrillator, that provides electrical signals to the heart 12 of the patient 14 via electrodes coupled to one or more of the leads 18, 20, 22 (e.g., electrodes that may be implanted in accordance with the description herein, such as, with use of non-invasive selection of implantation site regions).

The leads 18, 20, 22 extend into the heart 12 of the patient 14 to sense electrical activity of the heart 12 and/or to deliver electrical stimulation to the heart 12. In the example shown in FIG. 1, the right ventricular (RV) lead 18 extends through one or more veins (not shown), the superior vena cava (not shown), and the right atrium 26, and into the right ventricle 28. The left ventricular (LV) coronary sinus lead 20 extends through one or more veins, the vena cava, the right atrium 26, and into the coronary sinus 30 to a region adjacent to the free wall of the left ventricle 32 of the heart 12. The right atrial (RA) lead 22 extends through one or more veins and the vena cava, and into the right atrium 26 of the heart 12.

The IMD 16 may sense, among other things, electrical signals attendant to the depolarization and repolarization of the heart 12 via electrodes coupled to at least one of the leads 18, 20, 22. The IMD 16 may be configured to determine or identify effective electrodes located on the leads 18, 20, 22 using the exemplary methods and processes described herein. In some examples, the IMD 16 provides pacing therapy (e.g., pacing pulses) to the heart 12 based on the electrical signals sensed within the heart 12. The IMD 16 may be operable to adjust one or more parameters associated with the pacing therapy such as, e.g., AV delay and other various timings, pulse wide, amplitude, voltage, burst length, etc. Further, the IMD 16 may be operable to use various electrode configurations to deliver pacing therapy, which may be unipolar, bipolar, quadripoloar, or further multipolar. For example, a multipolar lead may include several electrodes that can be used for delivering pacing therapy. Hence, a multipolar lead system may provide, or offer, multiple electrical vectors to pace from. A pacing vector may include at least one cathode, which may be at least one electrode located on at least one lead, and at least one anode, which may be at least one electrode located on at least one lead (e.g., the same lead, or a different lead) and/or on the casing, or can, of the IMD. While improvement in cardiac function as a result of the pacing therapy may primarily depend on the cathode, the electrical parameters like impedance, pacing threshold voltage, current drain, longevity, etc. may be more dependent on the pacing vector, which includes both the cathode and the anode. The IMD 16 may also provide defibrillation therapy and/or cardioversion therapy via electrodes located on at least one of the leads 18, 20, 22. Further, the IMD 16 may detect arrhythmia of the heart 12, such as fibrillation of the ventricles 28, 32, and deliver defibrillation therapy to the heart 12 in the form of electrical pulses. In some examples, IMD 16 may be programmed to deliver a progression of therapies, e.g., pulses with increasing energy levels, until a fibrillation of heart 12 is stopped.

Figure 2A:
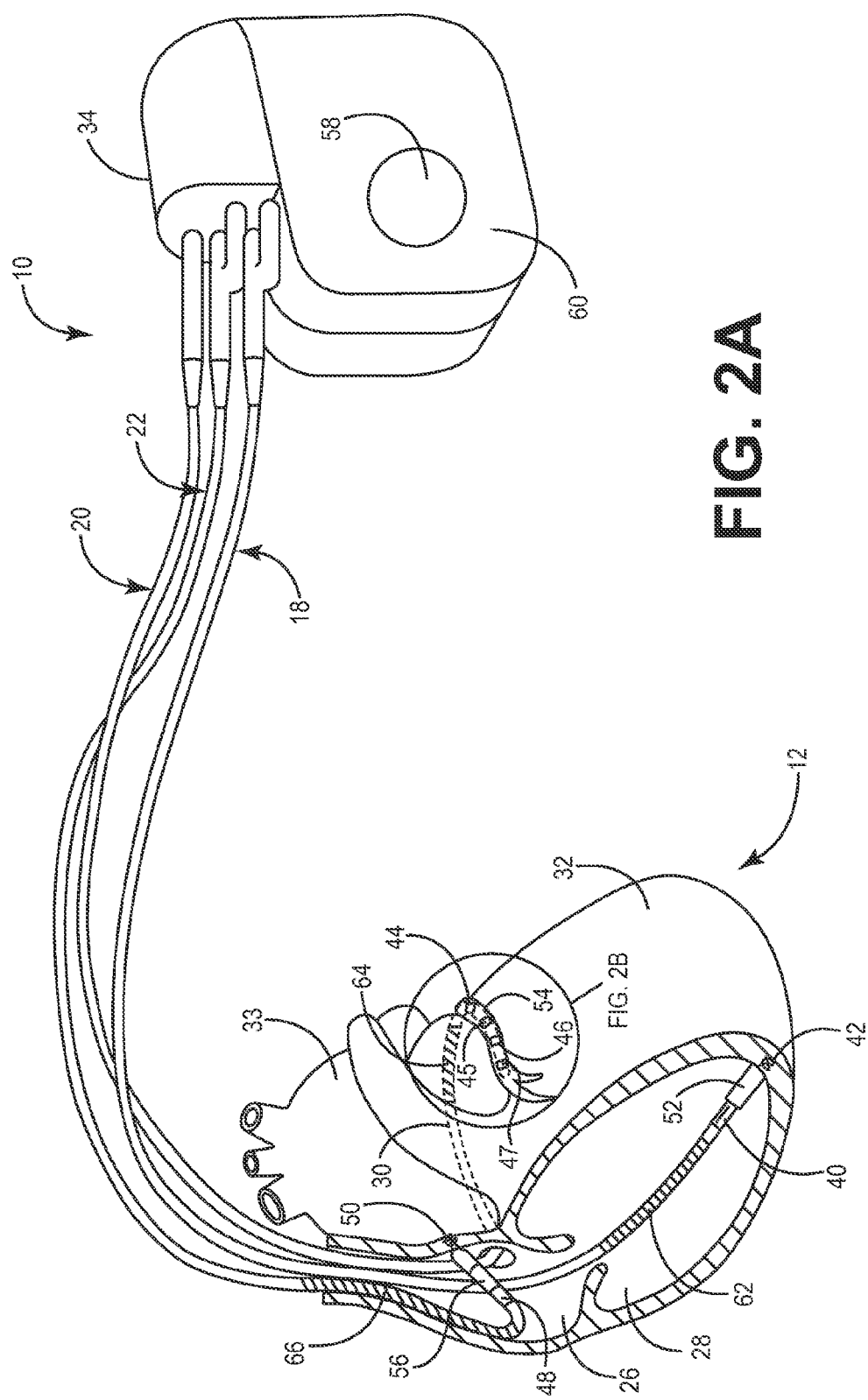
FIG. 2A is a diagram of the exemplary IMD of FIG. 1.
Figure 2B:
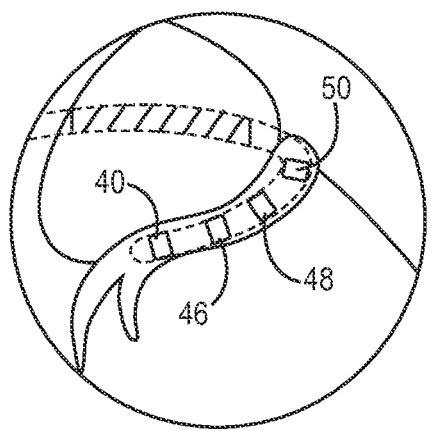
FIG. 2B is a diagram of an enlarged view of a lead distal end disposed in the left ventricle of FIG. 2A.

FIGS. 2A-2B are conceptual diagrams illustrating the IMD 16 and the leads 18, 20, 22 of therapy system 10 of FIG. 1 in more detail. The leads 18, 20, 22 may be electrically coupled to a therapy delivery module (e.g., for delivery of pacing therapy), a sensing module (e.g., for sensing one or more signals from one or more electrodes), and/or any other modules of the IMD 16 via a connector block 34. In some examples, the proximal ends of the leads 18, 20, 22 may include electrical contacts that electrically couple to respective electrical contacts within the connector block 34 of the IMD 16. A bipolar electrode is an electrode that can function as the anode of one pacing vector and the cathode of another pacing vector. An exemplary connector block (e.g. IS-4) can be seen with respect to U.S. Pat. No. 7,654,843 to Olson et al. issued Feb. 2, 2010, U.S. Pat. No. 7,601,033 to Ries et al. issued Oct. 13, 2009 and assigned to the assignee of the present invention, the disclosure of which are incorporated by reference in their entirety herein. In one or more embodiments, only one IS-4 connector is used since only four electrodes are connected to four conductors. However, if 8 individual electrodes were individually connected to eight conductors, then a bifurcated connector with two different bores could be used. The bifurcated connector with two different bores would employ the disclosure presented in U.S. Pat. No. 7,601,033. Specifically, a bifurcated connector with two individual IS-4 connectors or legs extending from the bifurcation can be used. In addition, in some examples, the leads 18, 20, 22 may be mechanically coupled to the connector block 34 with the aid of set screws, connection pins, or another suitable mechanical coupling mechanism.

Each of the leads 18, 20, 22 includes an elongated insulative lead body. As shown in FIG. 9, lead 20 optionally includes a monolithic controlled release device (MCRD) 112 (which is configured to release anti-bacterial agents over a period of time. The lead body 15 may carry a number of conductors (e.g., concentric coiled conductors, straight conductors, etc.) separated from one another by insulation (e.g., tubular insulative sheaths). In the illustrated example, bipolar electrodes 40, 142 are located proximate to a distal end of the lead 18. In addition, the bipolar electrodes 44, 45, 46, 47 are located proximate to a distal end of the lead 20 and the bipolar electrodes 48, 150 are located proximate to a distal end of the lead 22.

The electrodes 40, 44, 44, 45, 46, 47, 48 may take the form of ring electrodes, and the electrodes 142, 150 may take the form of extendable helix tip electrodes mounted retractably within the insulative electrode heads 52, 54, 56, respectively. Each of the electrodes 40, 42, 142, 44, 45, 46, 47, 48, 50, 150 may be electrically coupled to a respective one of the conductors (e.g., coiled and/or straight) within the lead body of its associated lead 18, 20, 22, and thereby coupled to respective ones of the electrical contacts on the proximal end of the leads 18, 20, 22.

At least four of the LV electrodes 40, 42, 44, 45, 46, 47, 48, 50, 52 (e.g. 40, 46, 48, and 50 shown in FIG. 2B) may be connected directly to four different conductors emanating from connector 34 (e.g. IS-4 connector etc.). The four different conductors (e.g. each individual polymeric coated filars present in a "multiconductor" conductor coil). Each individually insulated filars is a separate "conductor" and is crimped to each of the four contacts on the connector block 34.

The electrodes 40, 42, 142, 44, 45, 46, 47, 48, 50, 150, 52 may further be used to sense electrical signals (e.g., morphological waveforms within electrograms (EGM)) attendant to the depolarization and repolarization of the heart 12. The sensed electrical signals may be used to determine which of the electrodes 40, 42, 142, 44, 45, 46, 47, 48, 50, 52, 150 are the most effective in improving cardiac function. The electrical signals are conducted to the IMD 16 via the respective leads 18, 20, 22. In some examples, the IMD 16 may also deliver pacing pulses via the electrodes 40, 142, 44, 45, 46, 47, 48, 150 to cause depolarization of cardiac tissue of the patient's heart 12. In some examples, as illustrated in FIG. 2A, the IMD 16 includes one or more housing electrodes, such as housing electrode 58, which may be formed integrally with an outer surface of a housing 60 (e.g., hermetically-sealed housing) of the IMD 16 or otherwise coupled to the housing 60. Any of the electrodes 40, 42, 142, 44, 45, 46, 47, 48 and 50, 150, 52 may be used for unipolar sensing or pacing in combination with housing electrode 58. In other words, any of electrodes 40, 42, 142, 44, 45, 46, 47, 48, 50, 52, 150, 58 may be used in combination to form a sensing vector, e.g., a sensing vector that may be used to evaluate and/or analyze the effectiveness of pacing therapy. It is generally understood by those skilled in the art that other electrodes can also be selected to define, or be used for, pacing and sensing vectors. Further, any of electrodes 40, 42, 142, 44, 45, 46, 47, 48, 50, 52, 150, 58, which are not being used to deliver pacing therapy, may be used to sense electrical activity during pacing therapy.

Figure 3A:
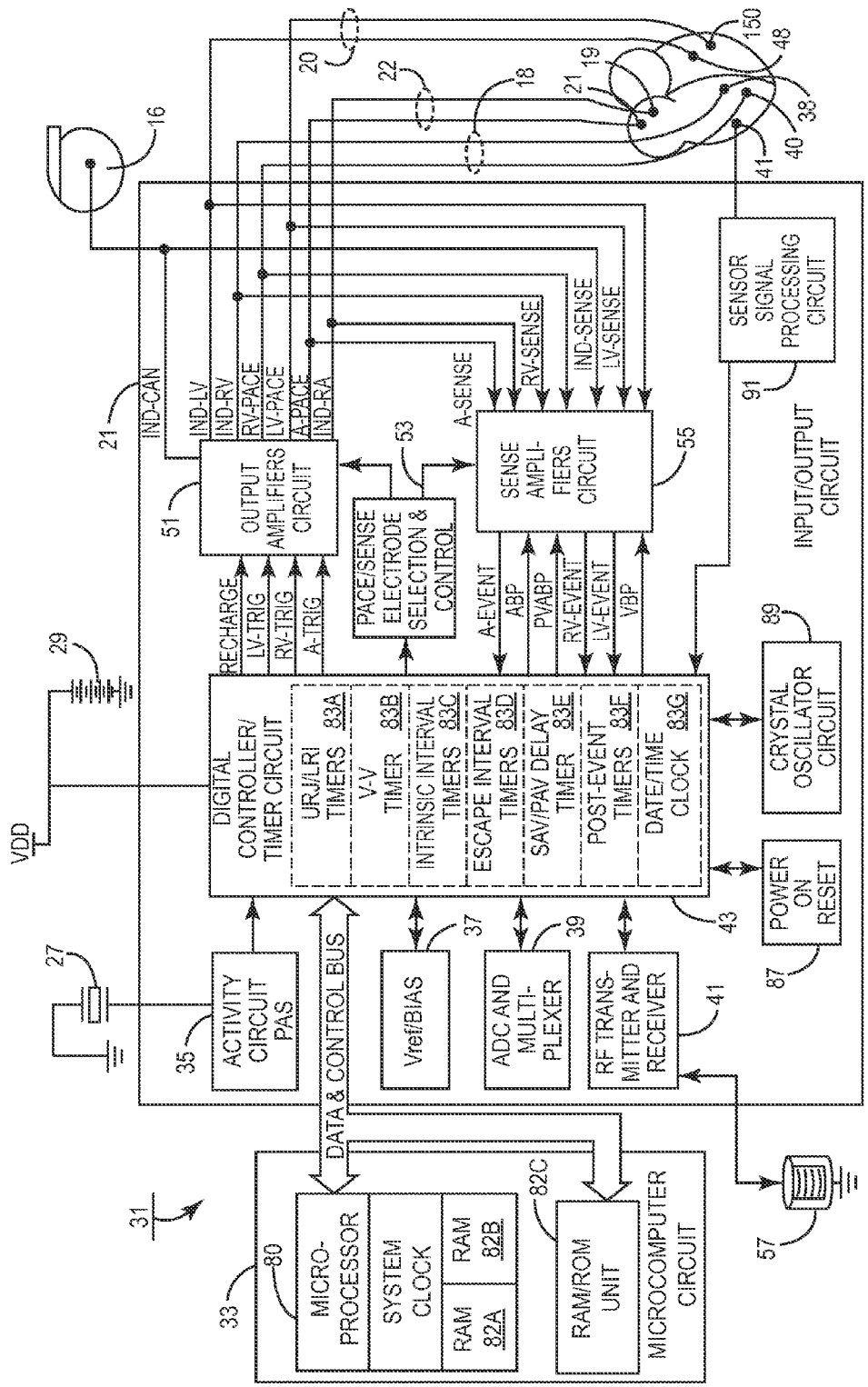
FIG. 3A is a block diagram of an exemplary IMD, e.g., the IMD of FIGS. 1-2.
Figure 3B:
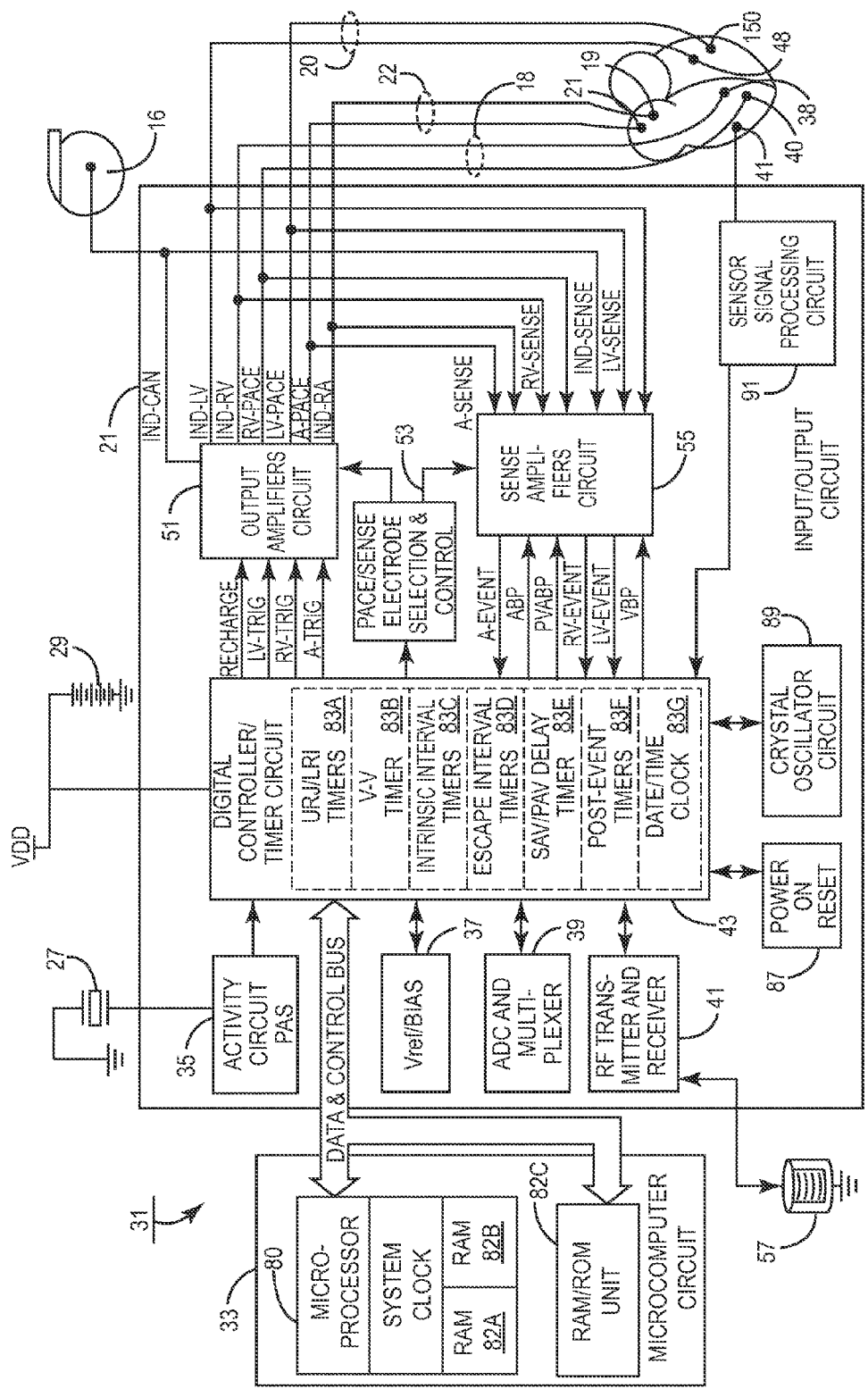
FIG. 3B is another block diagram of an exemplary IMD (e.g., an implantable pulse generator) circuitry and associated leads employed in the system of FIGS. 1-2 for providing three sensing channels and corresponding pacing channels.

As described in further detail with reference to FIG. 2A, the housing 60 may enclose a therapy delivery module that may include a stimulation generator for generating cardiac pacing pulses and defibrillation or cardioversion shocks, as well as a sensing module for monitoring the patient's heart rhythm. The leads 18, 20, 22 may also include elongated electrodes 62, 64, 66, respectively, which may take the form of a coil. The IMD 16 may deliver defibrillation shocks to the heart 12 via any combination of the elongated electrodes 62, 64, 66 and the housing electrode 58. The electrodes 58, 62, 64, 66 may also be used to deliver cardioversion pulses to the heart 12. Further, the electrodes 62, 64, 66 may be fabricated from any suitable electrically conductive material, such as, but not limited to, platinum, platinum alloy, and/or other materials known to be usable in implantable defibrillation electrodes. Since electrodes 62, 64, 66 are not generally configured to deliver pacing therapy, any of electrodes 62, 64, 66 may be used to sense electrical activity (e.g., for use in determining electrode effectiveness, for use in analyzing pacing therapy effectiveness, etc.) and may be used in combination with any of electrodes 40, 142, 44, 45, 46, 47, 48, 150, 58. In at least one embodiment, the RV elongated electrode 62 may be used to sense electrical activity of a patient's heart during the delivery of pacing therapy (e.g., in combination with the housing electrode 58 forming a RV elongated coil, or defibrillation electrode-to-housing electrode vector). It should be understood that merely a portion of the electrodes are placed in or near the heart and that more electrodes can be placed in the heart. The node (i.e. 150, 48) which refers to any point on a circuit where two or more circuit elements meet, is shown in FIGS. 3A-3B. The nodes were created from the electrodes and are merely exemplary in order to generally depict nodes. All of the possible nodes that can be made from lead 20 are not shown in order to avoid obscuring the invention.

The configuration of the exemplary therapy system 10 illustrated in FIGS. 1-3 is merely one example. In other examples, the therapy system may include epicardial leads and/or patch electrodes instead of or in addition to the transvenous leads 18, 20, 22 illustrated in FIG. 1. Further, in one or more embodiments, the IMD 16 need not be implanted within the patient 14. For example, the IMD 16 may deliver various cardiac therapies to the heart 12 via percutaneous leads that extend through the skin of the patient 14 to a variety of positions within or outside of the heart 12. In one or more embodiments, the system 10 may utilize wireless pacing (e.g., using energy transmission to the intracardiac pacing component(s) via ultrasound, inductive coupling, RF, etc.) and sensing cardiac activation using electrodes on the can/housing and/or on subcutaneous leads.

In other examples of therapy systems that provide electrical stimulation therapy to the heart 12, such therapy systems may include any suitable number of leads coupled to the IMD 16, and each of the leads may extend to any location within or proximate to the heart 12. For example, other examples of therapy systems may include three transvenous leads located as illustrated in FIGS. 1-3. Still further, other therapy systems may include a single lead that extends from the IMD 16 into the right atrium 26 or the right ventricle 28, or two leads that extend into a respective one of the right atrium 26 and the right ventricle 28.

FIG. 3A is a functional block diagram of one exemplary configuration of the IMD 16. As shown, the IMD 16 may include a control module 81, a therapy delivery module 84 (e.g., which may include a stimulation generator), a sensing module 86, and a power source 90.

The control module 81 may include a processor 80, memory 82, and a telemetry module 88. The memory 82 may include computer-readable instructions that, when executed, e.g., by the processor 80, cause the IMD 16 and/or the control module 81 to perform various functions attributed to the IMD 16 and/or the control module 81 described herein. Further, the memory 82 may include any volatile, non-volatile, magnetic, optical, and/or electrical media, such as a random access memory (RAM), read-only memory (ROM), non-volatile RAM (NVRAM), electrically-erasable programmable ROM (EEPROM), flash memory, and/or any other digital media. An exemplary capture management module may be the left ventricular capture management (LVCM) module described in U.S. Pat. No. 7,684,863 entitled "LV THRESHOLD MEASUREMENT AND CAPTURE MANAGEMENT" and issued Mar. 23, 2010, which is incorporated herein by reference in its entirety.

The processor 80 of the control module 81 may include any one or more of a microprocessor, a controller, a digital signal processor (DSP), an application specific integrated circuit (ASIC), a field-programmable gate array (FPGA), and/or equivalent discrete or integrated logic circuitry. In some examples, the processor 80 may include multiple components, such as any combination of one or more microprocessors, one or more controllers, one or more DSPs, one or more ASICs, and/or one or more FPGAs, as well as other discrete or integrated logic circuitry. The functions attributed to the processor 80 herein may be embodied as software, firmware, hardware, or any combination thereof.

The control module 81 may be used to determine the effectiveness of the electrodes 40, 42, 142, 44, 45, 46, 47, 48, 150, 58, 62, 64, 66 using the exemplary methods and/or processes described herein according to a selected one or more programs, which may be stored in the memory 82. Further, the control module 81 may control the therapy delivery module 84 to deliver therapy (e.g., electrical stimulation therapy such as pacing) to the heart 12 according to a selected one or more therapy programs, which may be stored in the memory 82. More, specifically, the control module 81 (e.g., the processor 80) may control various parameters of the electrical stimulus delivered by the therapy delivery module 84 such as, e.g., AV delays, pacing pulses with the amplitudes, pulse widths, frequency, or electrode polarities, etc., which may be specified by one or more selected therapy programs (e.g., AV delay adjustment programs, pacing therapy programs, pacing recovery programs, capture management programs, etc.). As shown, the therapy delivery module 84 is electrically coupled to electrodes 40, 42, 142, 44, 45, 46, 47, 48, 150, 58, 62, 64, 66, e.g., via conductors of the respective lead 18, 20, 22, or, in the case of housing electrode 58, via an electrical conductor disposed within housing 60 of IMD 16. Therapy delivery module 84 may be configured to generate and deliver electrical stimulation therapy such as pacing therapy to the heart 12 using one or more of the electrodes 40, 42, 142, 44, 45, 46, 47, 48, 150, 58, 62, 64, 66.

For example, therapy delivery module 84 may deliver pacing stimulus (e.g., pacing pulses) via ring electrodes 40, 44, 45, 46, 47, 48 coupled to leads 18, 20, and 22, respectively, and/or helical tip electrodes 142 and 150 of leads 18 and 22. Further, for example, therapy delivery module 84 may deliver defibrillation shocks to heart 12 via at least two of electrodes 58, 62, 64, 66. In some examples, therapy delivery module 84 may be configured to deliver pacing, cardioversion, or defibrillation stimulation in the form of electrical pulses. In other examples, therapy delivery module 84 may be configured deliver one or more of these types of stimulation in the form of other signals, such as sine waves, square waves, and/or other substantially continuous time signals.

The IMD 16 may further include a switch module 85 and the control module 81 (e.g., the processor 80) may use the switch module 85 to select, e.g., via a data/address bus, which of the available electrodes are used to deliver therapy such as pacing pulses for pacing therapy, or which of the available electrodes are used for sensing. The switch module 85 may include a switch array, switch matrix, multiplexer, or any other type of switching device suitable to selectively couple the sensing module 86 and/or the therapy delivery module 84 to one or more selected electrodes. More specifically, the therapy delivery module 84 may include a plurality of pacing output circuits. Each pacing output circuit of the plurality of pacing output circuits may be selectively coupled, e.g., using the switch module 85, to one or more of the electrodes 40, 42, 142, 44, 45, 46, 47, 48, 150, 58, 62, 64, 66 (e.g., a pair of electrodes for delivery of therapy to a pacing vector). In other words, each electrode can be selectively coupled to one of the pacing output circuits of the therapy delivery module using the switching module 85.

The sensing module 86 is coupled (e.g., electrically coupled) to sensing apparatus, which may include, among additional sensing apparatus, the electrodes 40, 42, 142, 44, 45, 46, 47, 48, 150, 58, 62, 64, 66 to monitor electrical activity of the heart 12, e.g., electrocardiogram (ECG)/electrogram (EGM) signals, etc. The ECG/EGM signals may be used to measure or monitor activation times (e.g., ventricular activations times, etc.), heart rate (HR), heart rate variability (HRV), heart rate turbulence (HRT), deceleration/acceleration capacity, deceleration sequence incidence, T-wave alternans (TWA), P-wave to P-wave intervals (also referred to as the P-P intervals or A-A intervals), R-wave to R-wave intervals (also referred to as the R-R intervals or V-V intervals), P-wave to QRS complex intervals (also referred to as the P-R intervals, A-V intervals, or P-Q intervals), QRS-complex morphology, ST segment (i.e., the segment that connects the QRS complex and the T-wave), T-wave changes, QT intervals, electrical vectors, etc.

The switch module 85 may be also be used with the sensing module 86 to select which of the available electrodes are used, or enabled, to, e.g., sense electrical activity of the patient's heart (e.g., one or more electrical vectors of the patient's heart using any combination of the electrodes 40, 42, 142, 44, 45, 46, 47, 48, 150, 52, 58, 62, 64, 66). Likewise, the switch module 85 may be also be used with the sensing module 86 to select which of the available electrodes are not to be used (e.g., disabled) to, e.g., sense electrical activity of the patient's heart (e.g., one or more electrical vectors of the patient's heart using any combination of the electrodes 40, 142, 44, 45, 46, 47, 48, 150, 58, 62, 64, 66), etc. In some examples, the control module 81 may select the electrodes that function as sensing electrodes via the switch module within the sensing module 86, e.g., by providing signals via a data/address bus.

In some examples, sensing module 86 includes a channel that includes an amplifier with a relatively wider pass band than the R-wave or P-wave amplifiers. Signals from the selected sensing electrodes may be provided to a multiplexer, and thereafter converted to multi-bit digital signals by an analog-to-digital converter for storage in memory 82, e.g., as an electrogram (EGM). In some examples, the storage of such EGMs in memory 82 may be under the control of a direct memory access circuit.

In some examples, the control module 81 may operate as an interrupt driven device, and may be responsive to interrupts from pacer timing and control module, where the interrupts may correspond to the occurrences of sensed P-waves and R-waves and the generation of cardiac pacing pulses. Any necessary mathematical calculations may be performed by the processor 80 and any updating of the values or intervals controlled by the pacer timing and control module may take place following such interrupts. A portion of memory 82 may be configured as a plurality of recirculating buffers, capable of holding one or more series of measured intervals, which may be analyzed by, e.g., the processor 80 in response to the occurrence of a pace or sense interrupt to determine whether the patient's heart 12 is presently exhibiting atrial or ventricular tachyarrhythmia.

The telemetry module 88 of the control module 81 may include any suitable hardware, firmware, software, or any combination thereof for communicating with another device, such as a programmer. For example, under the control of the processor 80, the telemetry module 88 may receive downlink telemetry from and send uplink telemetry to a programmer with the aid of an antenna, which may be internal and/or external. The processor 80 may provide the data to be uplinked to a programmer and the control signals for the telemetry circuit within the telemetry module 88, e.g., via an address/data bus. In some examples, the telemetry module 88 may provide received data to the processor 80 via a multiplexer.

During implanting of the implantable medical device and medical electrical lead or during a follow-up visit with a physician to check the implantable medical device and patient, medical personnel can employ a programmer. Programmers that may be used during implant can include the CARELINK ENCORE™ 29901 developed and sold by Medtronic, Inc. of Minneapolis, Minn. The programmer is configured to set one or a pair of electrodes as an anode or cathode using known techniques. Typically pacing is defined as tip-ring where the tip is the anode and ring is the cathode. Another example would be LVtip-RVring, or for high voltage shocks HVA-HVB where HVA is the device can shield and HVB is the RV coil. However, the present disclosure provides many more options. In addition or alternatively to conventional devices, the present disclosure is able to set one pair of electrodes as an anode or a cathode. Since four pairs of electrodes are located at the distal end of the lead, there are numerous options available for each pair of electrodes but for every pair electrodes designated as an anode, another pair of electrodes or another electrode must be present as a cathode. The optimal vector is selected by the doctor who may consider pacing capture threshold (PCT), impedance and/or phrenic nerve stimulation.

The various components of the IMD 16 are further coupled to a power source 90, which may include a rechargeable or non-rechargeable battery. A non-rechargeable battery may be selected to last for several years, while a rechargeable battery may be inductively charged from an external device, e.g., on a daily or weekly basis.

FIG. 3B is another embodiment of a functional block diagram for IMD 16. FIG. 3B depicts bipolar RA lead 22, bipolar RV lead 18, and bipolar LV CS lead 20 without the LA CS pace/sense electrodes and coupled with an implantable pulse generator (IPG) circuit 31 having programmable modes and parameters of a bi-ventricular DDD/R type known in the pacing art. In turn, the sensor signal processing circuit 91 indirectly couples to the timing circuit 83 and via data and control bus to microcomputer circuitry 33. The IPG circuit 31 is illustrated in a functional block diagram divided generally into a microcomputer circuit 33 and a pacing circuit 21. The pacing circuit 21 includes the digital controller/timer circuit 83, the output amplifiers circuit 51, the sense amplifiers circuit 55, the RF telemetry transceiver 41, the activity sensor circuit 35 as well as a number of other circuits and components described below.

Crystal oscillator circuit 89 provides the basic timing clock for the pacing circuit 21, while battery 29 provides power. Power-on-reset circuit 87 responds to initial connection of the circuit to the battery for defining an initial operating condition and similarly, resets the operative state of the device in response to detection of a low battery condition. Reference mode circuit 37 generates stable voltage reference and currents for the analog circuits within the pacing circuit 21, while analog to digital converter ADC and multiplexer circuit 39 digitizes analog signals and voltage to provide real time telemetry if a cardiac signals from sense amplifiers 55, for uplink transmission via RF transmitter and receiver circuit 41. Voltage reference and bias circuit 37, ADC and multiplexer 39, power-on-reset circuit 87 and crystal oscillator circuit 89 may correspond to any of those presently used in current marketed implantable cardiac pacemakers.

If the IPG is programmed to a rate responsive mode, the signals output by one or more physiologic sensor are employed as a rate control parameter (RCP) to derive a physiologic escape interval. For example, the escape interval is adjusted proportionally to the patient's activity level developed in the patient activity sensor (PAS) circuit 35 in the depicted, exemplary IPG circuit 31. The patient activity sensor 27 is coupled to the IPG housing and may take the form of a piezoelectric crystal transducer as is well known in the art and its output signal is processed and used as the RCP. Sensor 27 generates electrical signals in response to sensed physical activity that are processed by activity circuit 35 and provided to digital controller/timer circuit 83. Activity circuit 35 and associated sensor 27 may correspond to the circuitry disclosed in U.S. Pat. No. 5,052,388 entitled "METHOD AND APPARATUS FOR IMPLEMENTING ACTIVITY SENSING IN A PULSE GENERATOR" and issued on Oct. 1, 1991 and U.S. Pat. No. 4,428,378 entitled "RATE ADAPTIVE PACER" and issued on Jan. 31, 1984, each of which are incorporated herein by reference in their entireties. Similarly, the exemplary systems, apparatus, and methods described herein may be practiced in conjunction with alternate types of sensors such as oxygenation sensors, pressure sensors, pH sensors and respiration sensors, all well known for use in providing rate responsive pacing capabilities. Alternately, QT time may be used as the rate indicating parameter, in which case no extra sensor is required. Similarly, the exemplary embodiments described herein may also be practiced in non-rate responsive pacemakers.

Data transmission to and from the external programmer is accomplished by way of the telemetry antenna 57 and an associated RF transceiver 41, which serves both to demodulate received downlink telemetry and to transmit uplink telemetry. Uplink telemetry capabilities will typically include the ability to transmit stored digital information, e.g. operating modes and parameters, EGM histograms, and other events, as well as real time EGMs of atrial and/or ventricular electrical activity and marker channel pulses indicating the occurrence of sensed and paced depolarizations in the atrium and ventricle, as are well known in the pacing art.

Microcomputer 33 contains a microprocessor 80 and associated system clock and on-processor RAM and ROM chips 82A and 82B, respectively. In addition, microcomputer circuit 33 includes a separate RAM/ROM chip 82C to provide additional memory capacity. Microprocessor 80 normally operates in a reduced power consumption mode and is interrupt driven. Microprocessor 80 is awakened in response to defined interrupt events, which may include A-TRIG, RV-TRIG, LV-TRIG signals generated by timers in digital timer/controller circuit 83 and A-EVENT, RV-EVENT, and LV-EVENT signals generated by sense amplifiers circuit 55, among others. The specific values of the intervals and delays timed out by digital controller/timer circuit 83 are controlled by the microcomputer circuit 33 by way of data and control bus from programmed-in parameter values and operating modes. In addition, if programmed to operate as a rate responsive pacemaker, a timed interrupt, e.g., every cycle or every two seconds, may be provided in order to allow the microprocessor to analyze the activity sensor data and update the basic A-A, V-A, or V-V escape interval, as applicable. In addition, the microprocessor 80 may also serve to define variable, operative AV delay intervals and the energy delivered to each ventricle.

In one embodiment, microprocessor 80 is a custom microprocessor adapted to fetch and execute instructions stored in RAM/ROM unit 82 in a conventional manner. It is contemplated, however, that other implementations may be suitable to practice the present invention. For example, an off-the-shelf, commercially available microprocessor or microcontroller, or custom application-specific, hardwired logic, or state-machine type circuit may perform the functions of microprocessor 80.

Digital controller/timer circuit 83 operates under the general control of the microcomputer 33 to control timing and other functions within the pacing circuit 320 and includes a set of timing and associated logic circuits of which certain ones pertinent to the present invention are depicted. The depicted timing circuits include URI/LRI timers 83A, V-V delay timer 83B, intrinsic interval timers 83C for timing elapsed V-EVENT to V-EVENT intervals or V-EVENT to A-EVENT intervals or the V-V conduction interval, escape interval timers 83D for timing A-A, V-A, and/or V-V pacing escape intervals, an AV delay interval timer 83E for timing the A-LVp delay (or A-RVp delay) from a preceding A-EVENT or A-TRIG, a post-ventricular timer 83F for timing post-ventricular time periods, and a date/time clock 83G.

The AV delay interval timer 83E is loaded with an appropriate delay interval for one ventricular chamber (e.g., either an A-RVp delay or an A-LVp delay as determined using known methods) to time-out starting from a preceding A-PACE or A-EVENT. The interval timer 83E triggers pacing stimulus delivery, and can be based on one or more prior cardiac cycles (or from a data set empirically derived for a given patient).

The post-event timer 83F time out the post-ventricular time period following an RV-EVENT or LV-EVENT or a RV-TRIG or LV-TRIG and post-atrial time periods following an A-EVENT or A-TRIG. The durations of the post-event time periods may also be selected as programmable parameters stored in the microcomputer 33. The post-ventricular time periods include the PVARP, a post-atrial ventricular blanking period (PAVBP), a ventricular blanking period (VBP), a post-ventricular atrial blanking period (PVARP) and a ventricular refractory period (VRP) although other periods can be suitably defined depending, at least in part, on the operative circuitry employed in the pacing engine. The post-atrial time periods include an atrial refractory period (ARP) during which an A-EVENT is ignored for the purpose of resetting any AV delay, and an atrial blanking period (ABP) during which atrial sensing is disabled. It should be noted that the starting of the post-atrial time periods and the AV delays can be commenced substantially simultaneously with the start or end of each A-EVENT or A-TRIG or, in the latter case, upon the end of the A-PACE which may follow the A-TRIG. Similarly, the starting of the post-ventricular time periods and the V-A escape interval can be commenced substantially simultaneously with the start or end of the V-EVENT or V-TRIG or, in the latter case, upon the end of the V-PACE which may follow the V-TRIG. The microprocessor 80 also optionally calculates AV delays, post-ventricular time periods, and post-atrial time periods that vary with the sensor based escape interval established in response to the RCP(s) and/or with the intrinsic atrial rate.

The output amplifiers circuit 51 contains a RA pace pulse generator (and a LA pace pulse generator if LA pacing is provided), a RV pace pulse generator, and a LV pace pulse generator or corresponding to any of those presently employed in commercially marketed cardiac pacemakers providing atrial and ventricular pacing. In order to trigger generation of an RV-PACE or LV-PACE pulse, digital controller/timer circuit 83 generates the RV-TRIG signal at the time-out of the A-RVp delay (in the case of RV pre-excitation) or the LV-TRIG at the time-out of the A-LVp delay (in the case of LV pre-excitation) provided by AV delay interval timer 83E (or the V-V delay timer 83B). Similarly, digital controller/timer circuit 83 generates an RA-TRIG signal that triggers output of an RA-PACE pulse (or an LA-TRIG signal that triggers output of an LA-PACE pulse, if provided) at the end of the V-A escape interval timed by escape interval timers 83D.

The output amplifiers circuit 51 includes switching circuits for coupling selected pace electrode pairs from among the lead conductors and the IND_CAN electrode 20 to the RA pace pulse generator (and LA pace pulse generator if provided), RV pace pulse generator and LV pace pulse generator. Pace/sense electrode pair selection and control circuit 53 selects lead conductors and associated pace electrode pairs to be coupled with the atrial and ventricular output amplifiers within output amplifiers circuit 51 for accomplishing RA, LA, RV and LV pacing. The sense amplifiers circuit 55 contains sense amplifiers corresponding to any of those presently employed in contemporary cardiac pacemakers for atrial and ventricular pacing and sensing. High impedance P-wave and R-wave sense amplifiers may be used to amplify a voltage difference signal that is generated across the sense electrode pairs by the passage of cardiac depolarization wavefronts. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 83 controls sensitivity settings of the atrial and ventricular sense amplifiers 55.

The sense amplifiers are typically uncoupled from the sense electrodes during the blanking periods before, during, and after delivery of a pace pulse to any of the pace electrodes of the pacing system to avoid saturation of the sense amplifiers. The sense amplifiers circuit 55 includes blanking circuits for uncoupling the selected pairs of the lead conductors and the IND-CAN electrode 20 from the inputs of the RA sense amplifier (and LA sense amplifier if provided), RV sense amplifier and LV sense amplifier during the ABP, PVABP and VBP. The sense amplifiers circuit 55 also includes switching circuits for coupling selected sense electrode lead conductors and the IND-CAN electrode 20 to the RA sense amplifier (and LA sense amplifier if provided), RV sense amplifier and LV sense amplifier. Again, sense electrode selection and control circuit 53 selects conductors and associated sense electrode pairs to be coupled with the atrial and ventricular sense amplifiers within the output amplifiers circuit 51 and sense amplifiers circuit 55 for accomplishing RA, LA, RV and LV sensing along desired unipolar and bipolar sensing vectors.

Right atrial depolarizations or P-waves in the RA-SENSE signal that are sensed by the RA sense amplifier result in a RA-EVENT signal that is communicated to the digital controller/timer circuit 83. Similarly, left atrial depolarizations or P-waves in the LA-SENSE signal that are sensed by the LA sense amplifier, if provided, result in a LA-EVENT signal that is communicated to the digital controller/timer circuit 83. Ventricular depolarizations or R-waves in the RV-SENSE signal are sensed by a ventricular sense amplifier result in an RV-EVENT signal that is communicated to the digital controller/timer circuit 83. Similarly, ventricular depolarizations or R-waves in the LV-SENSE signal are sensed by a ventricular sense amplifier result in an LV-EVENT signal that is communicated to the digital controller/timer circuit 83. The RV-EVENT, LV-EVENT, and RA-EVENT, LA-SENSE signals may be refractory or non-refractory, and can inadvertently be triggered by electrical noise signals or aberrantly conducted depolarization waves rather than true R-waves or P-waves.

The techniques described in this disclosure, including those attributed to the IMD 16, the computing apparatus 140, and/or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Figure 6:
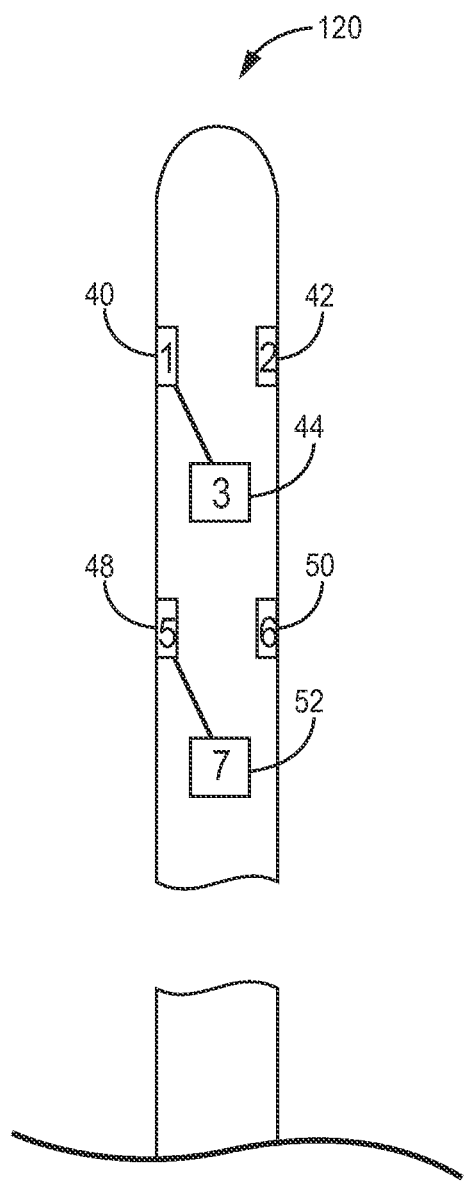
FIG. 6 is a schematic diagram of the lead distal end depicted in FIG. 4 rotated clockwise by 45 degrees away from the front position shown in FIG. 4.
Figure 7:
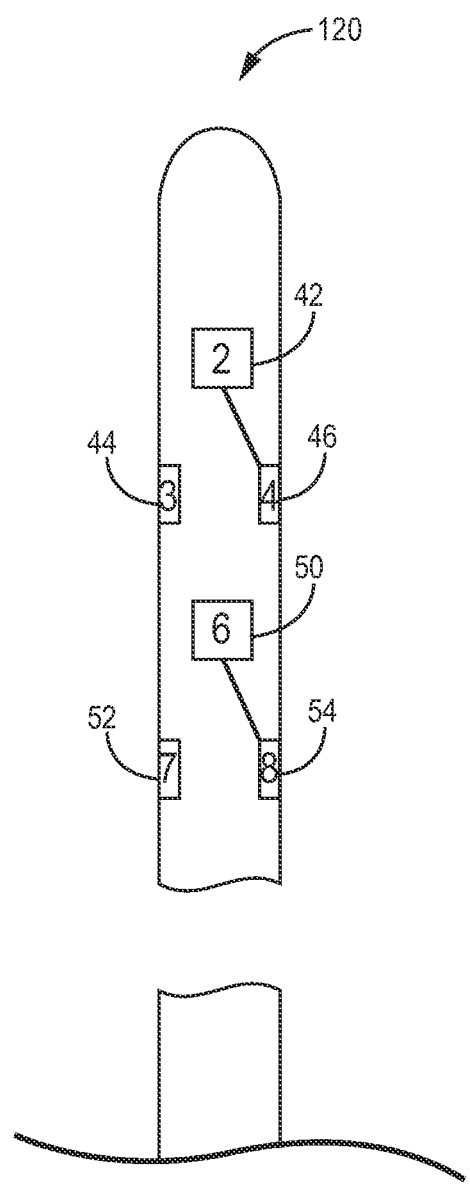
FIG. 7 is a schematic diagram of a back view of the lead distal end rotated clockwise by 45 degrees away from the position shown in FIG. 6.
Figure 8:
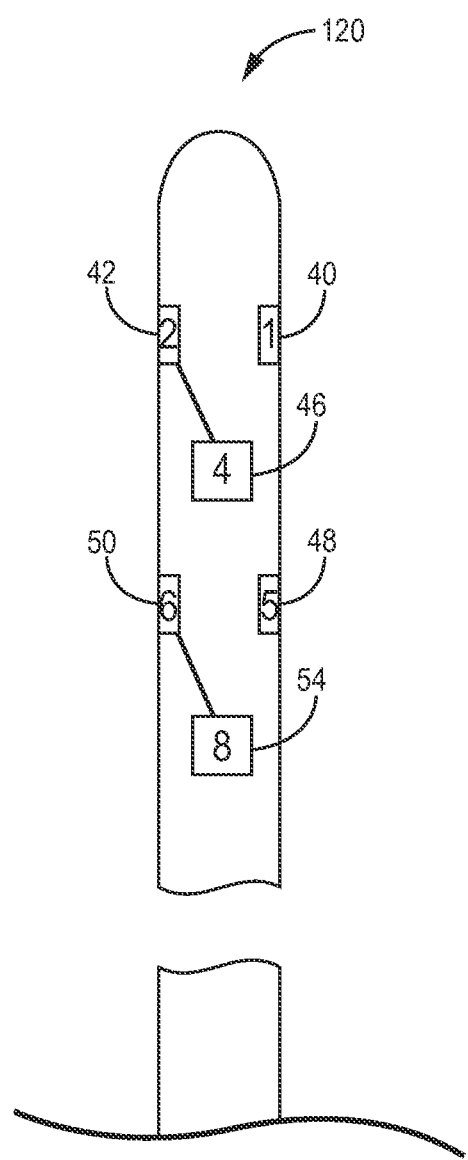
FIG. 8 is a schematic diagram of the distal end of the lead rotated clockwise by 45 degrees away from the position shown in FIG. 7.

FIGS. 4, and 6-8 generally depict electrodes 40, 42, 44, 46, 48, 50, 52, and 54 placed along a distal end 120 of lead 20. Since the electrodes 40, 42, 44, 46, 48, 50, 52, and 54 are placed around the circumference of the distal end 120, the distal end 120 is shown through a 360 degree clockwise rotation by FIGS. 4, and 6-8 order to show the placement of each electrode. For example, FIG. 4 depicts a front view of the distal end 20 while FIG. 6 shows lead 20 rotated 90 degrees in a clockwise direction from the front view of FIG. 4. FIG. 7 shows a back view of lead 20 depicted in FIG. 4, which is lead 20 rotated 90 degrees in a clockwise direction from the distal end 20 shown in FIG. 6. FIG. 8 depicts lead 20 rotated 90 degrees in a clockwise direction from the position of the lead 20 depicted in FIG. 7.

First and second electrodes 40, 42 are located along the same lead body 15 length but are diametrically opposed (180 degrees apart from each other) to one another as shown by the front and back views of FIGS. 4 and 7, respectively and the top down view of FIG. 5. First and fifth electrodes 40, 48 are aligned or substantially aligned (i.e. within about 0.1 cm to about 0.2 cm of exact alignment) along the longitudinal axis 118 but the first and fifth electrodes are separated along the lead body length by about 3.95 cm to about 4.0 cm. The first and third electrodes 40, 44 are circumferentially shifted or rotationally separated by about 90 degrees as shown in FIG. 4. The first and fourth electrodes 40, 46 are also circumferentially shifted or rotationally separated by about 90 degrees as shown in FIG. 4. The first and third electrodes 40, 44 as well as the first and fourth electrodes 40, 46 are spaced apart along the longitudinal axis 118 by about L2 (e.g. 1.2 cm).

The third electrode 44 is circumferentially shifted by about 90 degrees away from the first and second electrodes 40, 42 respectively along the distal end 120. On the proximal end of the electrodes, third electrode 44 is circumferentially shifted away from fifth and sixth electrodes 48, 50 as shown in FIG. 6. The third electrode is a distance of L2 along the lead body length away from the first and second electrodes 40, 42 and L4 distance away from the fifth and sixth electrodes 48, 50.

Third and fourth electrodes 44, 46 are located along the same lead body 15 length as shown in FIGS. 4 and 7. Moreover, third and fourth electrodes 44, 46 are diametrically opposed to each other (circumferentially shifted 180 degrees away from each other). Additionally, third and fourth electrodes 44, 46 extend about 1 cm distance away from the distal tip 314 (FIG. 9) and toward the proximal end of lead 20.

Fifth and sixth electrodes 48, 50 are diametrically opposed to one another (i.e. 180 degrees away from each other). The fifth electrode 48 is circumferentially shifted about 90 degrees away from third and fourth electrodes 44, 46, respectively. Fifth electrode 48 is about L4 distance along the lead body length away from third and fourth electrodes 44, 46, respectively and L6 distance along the lead body length from the seventh and eight electrodes 52, 54, respectively.

The electrodes at the distal end 120 extend a total body length $L_{Total}$ of about 4.3 cm, which is the sum of L1, L2, L3, L4, L5, L6 and L7. In one or more embodiments, the length of each electrode, represented by L1, L3, L5, and L7, is about 0.175 mm. L1, L3, L5, and L7 represent the distance between the electrodes along the length of the lead body 15. L1, L3, L5, and L7 are each equal to about 0.175 mm. L2, L4 and L6, representing the space between electrodes, are each equal to about 1.2 cm.

Left ventricular electrodes 40, 42, 44, 46, 48, 50, 52, and 54, are electrically paired in a diagonally and circumferentially shifted (or angularly displaced) configuration in order to provide multi-electrode pacing vectors (e.g. up to four multi-site pacing vectors. The electrical connection can be made by a jumper which is a short length electrical conductor used to close a break in, or bypass part of, an electrical circuit. As shown, each jumper can range from about 1 cm to about 2 cm in length.

Four of the eight electrodes are connected to conductors in connector block 34. For example, the first conductor, which extends through the IS-4 connector block 34 is connected first electrode 40. First electrode 40 is also electrically connected to third electrode 44. The second conductor, which extends into or through the IS-4 connector block 34, is connected to second electrode 42. The second electrode is jumpered to the fourth electrode 46. The third conductor extends into or through the IS-4 connector block 34 and connects with the fifth electrode 48. The fifth electrode is jumpered to the seventh electrode 52. The fourth conductor extends through the IS-4 connector block 34 and connects with the sixth electrode 50. The sixth electrode 50 is jumpered to the eighth electrode 54.

First, second, fifth and sixth electrodes 40, 42, 48, 50 in combination with first through four conductors passing through connector module 34 (e.g. IS-4 connector etc.) form four different electronic circuits. For example, a first circuit comprises a first electrode, a third electrode jumpered to the first electrode, all of which are electronically connected to a first conductor passing through the connector module 34. A second circuit comprises a second electrode 42, a fourth electrode 46 jumpered to the second electrode 42, all of which are electronically connected to a second conductor passing through the connector block 34. A third circuit comprises a fifth electrode 48 connected to a seventh electrode 52 which are electronically connected to a third conductor passing through the connector module 34. A fourth circuit comprises a sixth electrode 50 connected to an eighth electrode 54, all of which and connected to a fourth conductor passing through the connector block 34.

As previously mentioned relative to FIG. 3, the implantable medical device control circuit automatically selects the most appropriate place from which to deliver stimuli to cardiac tissue after the implantable medical device has been chronically implanted. However, when the physician is implanting the implantable medical device, a programmer is used with computer instructions to determine which diagonal electrodes are optimal for a patient.

An implantable medical device control circuit is used to activate and/or deactivate each pair of electrodes. In one embodiment, only one of the pair of electrodes is active at any given time. In another embodiment, one or more pairs of electrodes can be activated depending upon the condition of the cardiac tissue.

Presented below is Table 1 that shows the pacing vectors that may be attained through implementing the diagonal directional electrodes on the distal end of the lead 20. The truth table indicates which electrodes can be activated ("1") for delivering therapy and/or sensing from the electrodes. Deactivated electrodes are indicated by "0". Only four primary electrodes on lead 20 are shown in the table. Primary electrodes are those electrodes directly connected with a conductor extending from the connector block 34. It should be understood that if one of the primary electrodes such as the first, second, fifth, and sixth electrodes 40, 42, 48, 50 are activated, the electrodes jumpered to each electrode is also activated. For example, if the first electrode 40 is delivering stimuli to cardiac tissue, then the third electrode 44 is also delivering stimuli to the cardiac tissue due to the electrical connection between the first and third electrodes 40, 44.

TABLE 1

Pacing vectors formed by diagonally connected electrodes

| Pacing vectors | Electrode connected to conductor 1 | Electrode connected to conductor 2 | Electrode connected to conductor 3 | Electrode connected to conductor 4 |
|---|---|---|---|---|
| 1 | 0 | 0 | 0 | 0 |
| 2 | 0 | 0 | 0 | 1 |
| 3 | 0 | 0 | 1 | 0 |
| 4 | 0 | 0 | 1 | 1 |
| 5 | 0 | 1 | 0 | 0 |
| 6 | 0 | 1 | 0 | 1 |
| 7 | 0 | 1 | 1 | 0 |
| 8 | 0 | 1 | 1 | 1 |
| 9 | 1 | 0 | 0 | 0 |
| 10 | 1 | 0 | 0 | 1 |
| 11 | 1 | 0 | 1 | 0 |
| 12 | 1 | 0 | 1 | 1 |
| 13 | 1 | 1 | 0 | 0 |
| 14 | 1 | 1 | 0 | 1 |
| 15 | 1 | 1 | 1 | 0 |
| 16 | 1 | 1 | 1 | 1 |

In yet another example, the electrode pairs on lead 20 in which four electrodes are able to deliver electrical stimulation in diagonal direction using only 2 pacing circuits. For example, assume a first pair of electrodes (e.g. electrodes 2 and 4) and second pair of electrodes (e.g. electrodes 6 and 8) were placed towards the myocardial side of the heart while third pair of electrodes (e.g. electrodes 1 and 3) and fourth pair of electrodes (e.g. electrodes 5 and 7) located on the pericardial side of the heart.

Figure 11:
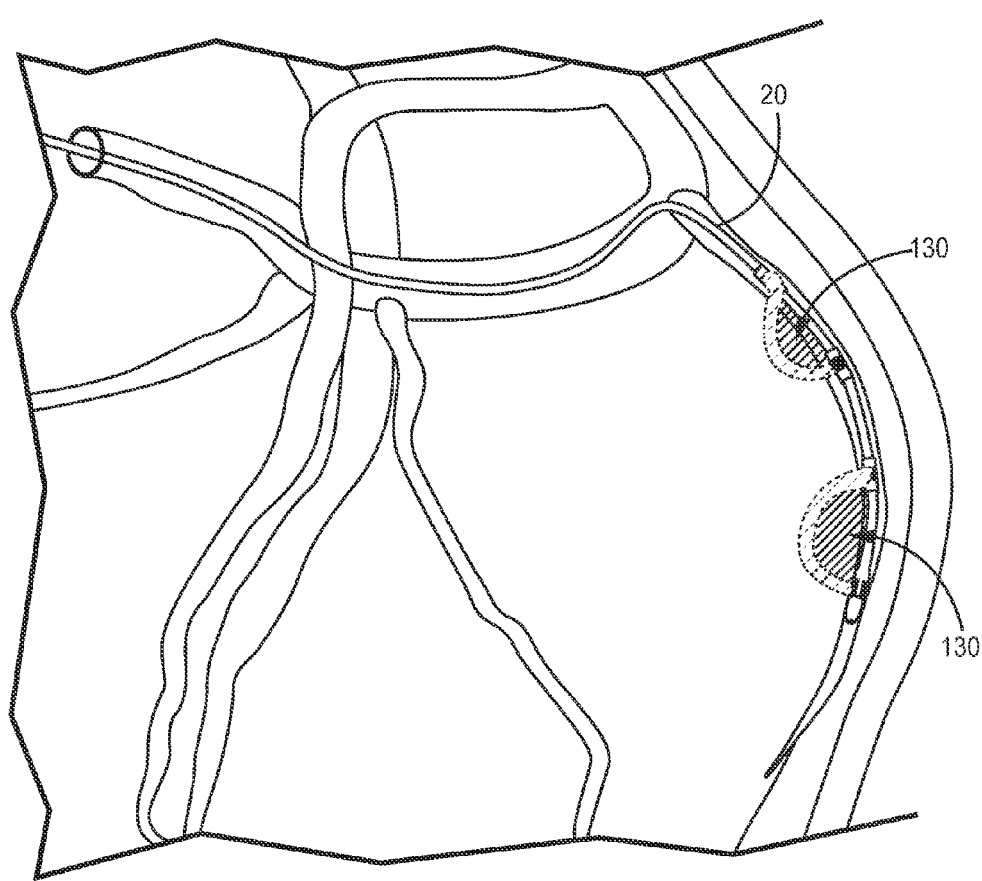
FIG. 11 is a schematic diagram of a human heart and of the lead through the coronary sinus as implanted along with electrical stimulation fields created from the electrodes on the lead.

Numerous methods exist for placing lead 20 near and/or into excitable tissue (e.g. cardiac tissue such as myocardial tissue). One such method 200, depicted in FIG. 12, describes lead placement corresponding to the positioning of the lead 20 as illustrated in FIG. 11. A lead delivery device (e.g. stylet, guide wire, hybrid guidewire/stylet etc.), such as the ATTAIN HYBRID®, is inserted into an aperture at a proximal end of lead 20. Lead 20 is then inserted directly through an integrated valve of a guide catheter such as ATTAIN CATHETER® developed and sold by Medtronic, Inc. of Minneapolis, Minn. Lead 20 is introduced into the vascular system (step 202, FIG. 12) by any conventional technique. The lead 20 is then moved into the vasculature (e.g. coronary venous system etc.) to a desired location, for example by advancing the lead body 15 by means of the guide catheter. The coronary venous system includes the coronary sinus vein, great cardiac vein, middle cardiac vein, left posterior ventricular vein, and/or any other applicable cardiac veins. Lead 20 passes through the coronary sinus and into a cardiac vein extending therefrom, while substantially maintaining lead body 15 shape.

The lead 20 is then advanced further into the coronary venous system (Step 204, FIG. 12) and generally travels in a downward path of the coronary vein along the naturally curved shape of the heart. This may be accomplished by passing the lead 20 through a guide catheter, or by advancing the lead 20 over a guidewire or by means of a stylet inserted into the lead 20. A hybrid guidewire/stylet may also be used to place a lead 20 near or adjacent myocardial tissue. Any conventional mechanism for placing the lead 20 into and within the coronary venous system may be employed.

Figure 12:
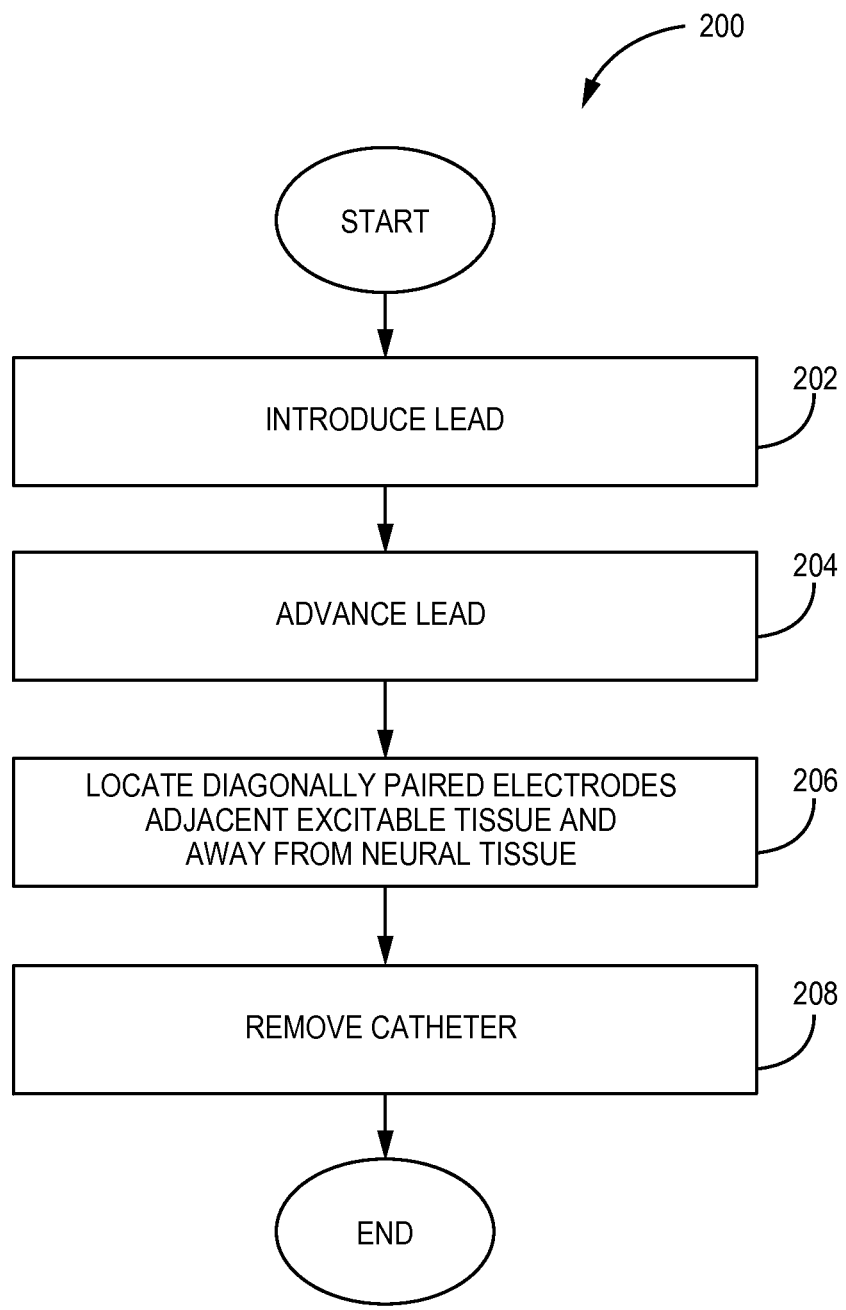
FIG. 12 is a flow chart illustrating the steps of implantation of a lead according to the present disclosure.

Lead 20 is located at an appropriate location, as determined by the physician (Step 206, FIG. 12). Thereafter, the lead body 15 may be moved (i.e. advanced and/or retracted) through the guide catheter until the diagonally paired electrodes are located in a desirable position (Step 206, FIG. 12). According to one embodiment, a first and second pair of diagonally paired electrodes are used. According to another embodiment, a first, second and third pair of diagonally paired electrodes are used. According to yet another embodiment, a first, second, third and fourth pair of diagonally paired electrodes are used. Determination of the position for electrode location may be accomplished by any conventional method, such as pacing threshold testing and/or measurement of R-wave amplitudes. The guide catheter analyzer cable interface is useful to perform this function. Alternatively or additionally, appropriate electrode locations may also be determined based upon determinations of hemodynamic characteristics of the heart as associated with stimulation of heart tissue at various electrode locations.

Figure 13:
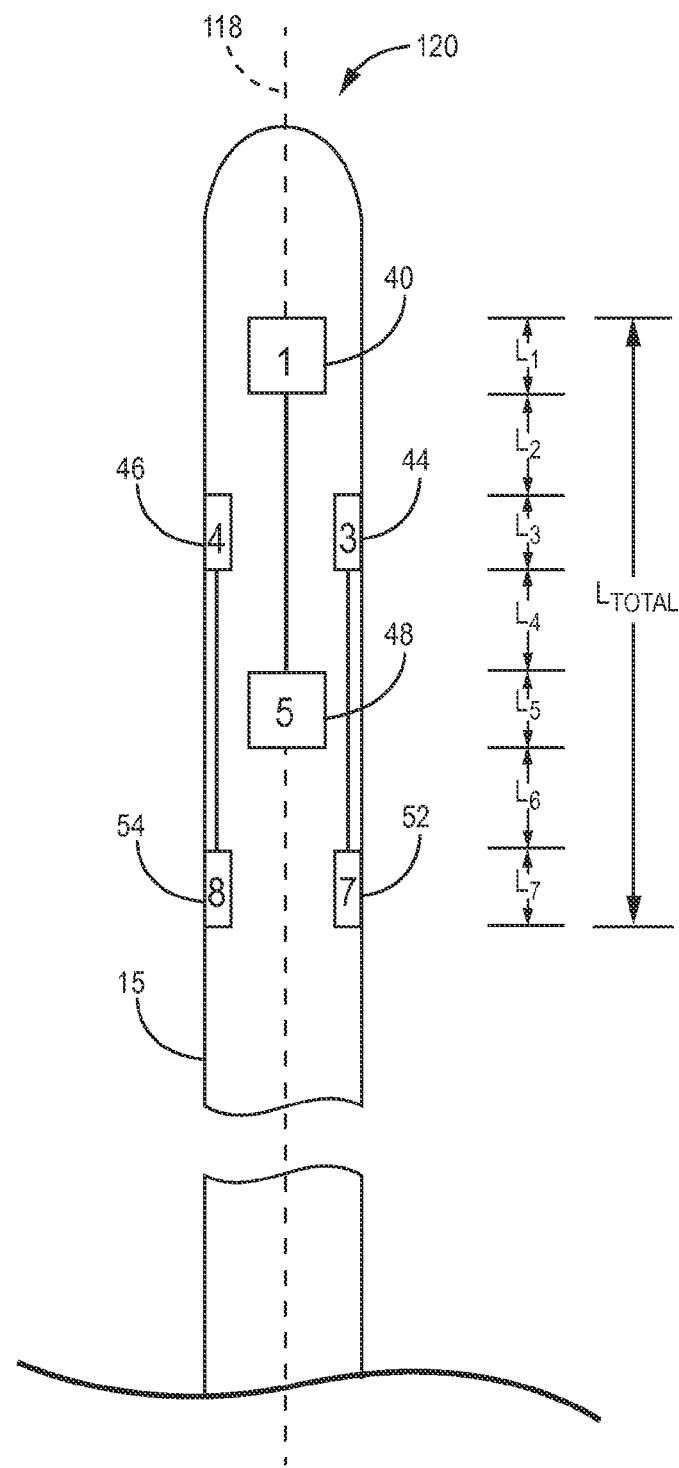
FIG. 13 is an alternative embodiment a front view of a set of electrodes positioned along a distal end of a lead such that the diagonal electrodes are connected along a vertical longitudinal line.
Figure 14:
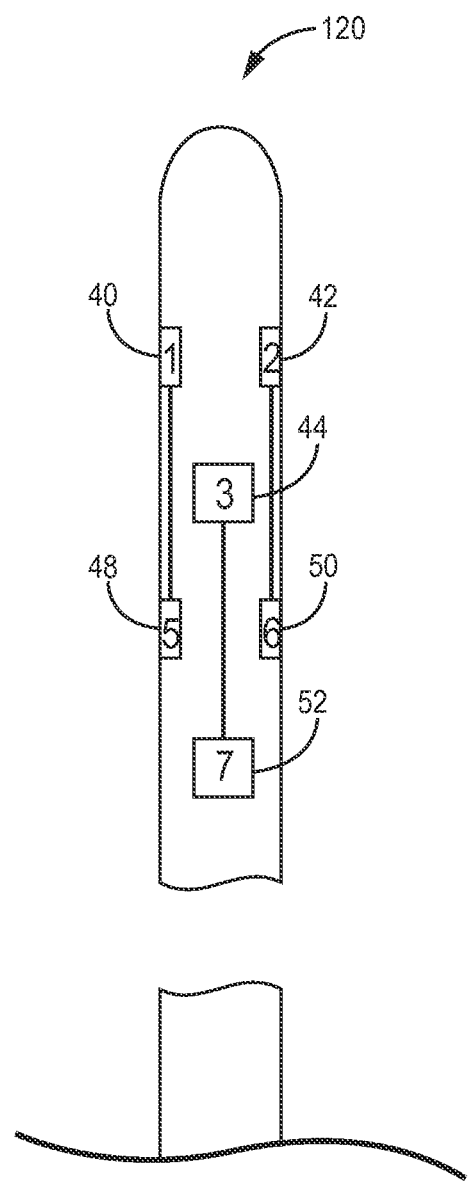
FIG. 14 is a schematic diagram of the lead distal end depicted in FIG. 13 rotated clockwise by 45 degrees away from the front position shown in FIG. 13.

FIGS. 13 and 14 depict an alternate embodiment to FIGS. 4, 6-8. Each electrode in FIGS. 13 and 14 is in the same position as described relative to FIGS. 4, 6-8 but the electrical connection between each electrode is different. FIG. 13 is a front view while FIG. 14 is rotated clockwise by 45 degrees away from the front position shown in FIG. 13. Four of the eight electrodes are connected to conductors in connector block 34. For example, the first conductor, which extends through the IS-4 connector block 34 is connected first electrode 40. First electrode 40 is also electrically connected to fifth electrode 48. The second conductor, which extends into or through the IS-4 connector block 34, is connected to second electrode 42. The second electrode is jumpered to the sixth electrode 50. The third conductor extends into or through the IS-4 connector block 34 and connects with the third electrode 44. The third electrode 44 is jumpered to the seventh electrode 52. The fourth conductor extends through the IS-4 connector block 34 and connects with the fourth electrode 46. The fourth electrode 46 is jumpered to the eighth electrode 54. Although the electrodes are diagonally located around the distal end of the lead, as shown in FIGS. 13-14, a linear connection along the longitudinal axis exists between each electrode for each electrode pair. The embodiment shown in FIGS. 13-14 is able to achieve a minimum of 16 pacing vectors.

The present disclosure, directed to pairs of diagonally directional electrodes, located on a single lead and directly connected to a IS-4 connector module, can selectively deliver electrical stimulation and/or sense physiological signals from the patient. By doing so, the spatially separated electrode pair configuration shown in FIGS. 4-9 achieves improved electrical stimulation fields compared to conventionally placed electrodes. For example, the diagonally paired electrodes generate an electrical stimulation field 130 (FIG. 11) that is generally rounded, and elliptical in nature which is substantially different in shape compared to the electrical stimulation field generated by a conventional electrode configuration. The electrical stimulation field may be smaller in shape as shown in FIG. 11 than conventional electrical stimulation fields but sufficiently large to capture cardiac tissue while avoiding unnecessarily stimulating other cardiac tissue.

Many alternatives leads can employ the teaching disclosed herein. For example, alternative medical electrical leads can include active or passive fixation mechanisms (e.g. helix, tines, adhesive etc.). Additionally, while the lead is described as advancing through the coronary sinus, it should be understood that other locations in the heart's venous system may also be accessed using this lead. Electrode placement may alternatively be optimized for atrial stimulation and/or sensing. Alternatively, the lead may be useful in other vascular or non-vascular location within the body wherein the distance between a suitable fixation location and a desired electrode location may be variable. Additionally, while the invention has been described with respect to lead 20, the invention can be applied to other cardiac leads or neurological leads.

Finally, the primary electrodes are described as the first, second, fifth, and sixth electrodes 40, 42, 48, 50, any one/or combination of electrodes can be designated as primary electrodes. As previously stated, primary electrode is an electrode directly connected to the conductor extending from the connector block 34.

The following paragraphs enumerated consecutively from 1 through 24 provide for various aspects of the present disclosure. In one embodiment in a first paragraph (1) the present disclosure provides:

1. A implantable medical device comprising:
   a housing;
   a connector block coupled to the housing;
   a medical electrical lead coupled to the connector block, the lead comprising an elongated lead body having a length between a proximal end and a distal end with a longitudinal axis extending between the proximal end and the distal end,
   a plurality of electrodes, located along the distal end of the lead body, the plurality of electrodes parsed into a first and second pair electrodes in which the first pair of electrodes comprising a first electrode electrically connected to a second electrode while diagonally and circumferentially spaced apart, and the second pair of electrodes comprising a third electrode electrically connected to a fourth electrode while diagonally and circumferentially spaced apart;
   a first conductor extending from the connector block and directly connected to one of the first and second electrodes; and
   a second conductor extending from the connector block and directly connected to one of the third and fourth electrodes.

2. The device according to paragraph 1 wherein the first pair of electrodes configured to be one of an anode and a cathode.

3. The device according to any of paragraphs 1-2 wherein the second pair of electrodes configured to be one of an anode and a cathode, wherein the second pair of electrodes dependent upon whether the first pair of electrodes configured to be one of an anode and a cathode.

4. The device according to any of paragraphs 1-3 wherein the plurality of electrodes further comprising a third pair of electrodes comprising a fifth electrode and a sixth electrode diagonally spaced apart from each other and electrically connected.

5. The device according to any of paragraphs 3-4 wherein the plurality of electrodes further comprising a fourth pair of electrodes comprising a seventh electrode and a eighth electrode diagonally spaced apart from each other and electrically connected.

6. The device according to any of paragraphs 3-5 wherein the plurality of electrodes further comprising a fourth pair of electrodes configured to be set as one of an anode and a cathode.

7. The device according to any of paragraphs 1-6, wherein the plurality of electrodes located solely on a distal end of the lead forms a minimum of 16 pacing vectors.

8. The device according to any of paragraphs 1-7, wherein the plurality of electrodes located solely on a distal end of the lead forms a minimum of 12 or more pacing vectors.

9. The device according to any of paragraphs 1-8, wherein the plurality of electrodes located solely on a distal end of the lead forms a minimum of 8 or more pacing vectors.

10. The device according to any of paragraphs 1-9, wherein the plurality of electrodes located solely on a distal end of the lead forms a minimum of 4 or more pacing vectors.

11. A medical electrical lead of any of paragraphs 1-10, wherein the first pair of electrodes being diagonally electrically connected.

12. A medical electrical lead of any of paragraphs 1-11, wherein the second pair of electrodes being diagonally electrically connected.

13. A medical electrical lead of any of paragraphs 1-9, wherein the first electrode is linearly connected to the second electrode.

14. A medical electrical lead of any of paragraphs 1-9, wherein the third electrode is linearly connected to the fourth electrode.

15. A method of implanting a medical electrical lead in a patient's body, comprising:
    advancing, within in the patient's body, a lead having an elongated lead body defining a longitudinal axis and carrying a set of electrodes circumferentially and diagonally spaced apart, the set of electrodes parsed into pairs of electrodes; and
    moving the lead body through a coronary vein and placing the lead into excitable tissue and avoiding neural tissue.

16. A method according to paragraph 15 wherein a first pair of electrodes comprising electrodes being diagonally electrically connected.

17. A method according to any of paragraphs 15-16, wherein a second pair of electrodes being diagonally electrically connected.

18. A method according to any of paragraphs 15-17, wherein a first pair of electrodes comprising a first electrode linearly electrically connected to a second electrode.

19. A method according to any of paragraphs 15-18, wherein a second pair of electrodes comprising a third electrode linearly electrically connected to a fourth electrode.

20. A system of using a medical electrical lead in a patient's body, comprising:
    means for advancing, within in the patient's body, a lead having an elongated lead body defining a longitudinal axis and carrying a set of electrodes circumferentially and diagonally spaced apart, the set of electrodes parsed into pairs of electrodes;
    means for moving the lead body through a coronary vein and placing the lead into excitable tissue and avoiding neural tissue.

21. A system according to paragraph 20 wherein a first pair of electrodes comprising electrodes being diagonally electrically connected.

22. A system according to paragraph 20, wherein a second pair of electrodes being diagonally electrically connected.

23. A system according to paragraph 20 wherein a first pair of electrodes comprising a first electrode linearly electrically connected to a second electrode.

24. A system according to paragraph 20, wherein a second pair of electrodes comprising a third electrode linearly electrically connected to a fourth electrode.

In the foregoing detailed description, the invention has been described with reference to specific embodiments. However, it may be appreciated that various modifications and changes can be made without departing from the scope of the invention as set forth in the appended claims.

The invention claimed is:

1. A implantable medical device comprising:
   a housing;
   a connector block coupled to the housing;
   a medical electrical lead coupled to the connector block, the lead comprising an elongated lead body having a length between a proximal end and a distal end with a longitudinal axis extending between the proximal end and the distal end,
   a plurality of electrodes, located along the distal end of the lead body, the plurality of electrodes parsed into first and second pair electrodes in which the first pair of electrodes comprising a first electrode electrically connected to a second electrode by means of a first jumper conductor within the lead body while diagonally and circumferentially spaced apart, and the second pair of electrodes comprising a third electrode electrically connected to a fourth electrode by means of a second jumper conductor within the lead body while diagonally and circumferentially spaced apart;
   a first conductor extending from the connector block and directly connected to one of the first and second electrodes; and
   a second conductor extending from the connector block and directly connected to one of the third and fourth electrodes, wherein the first pair of electrodes is electrically connected together as one of either an anode or a cathode, and wherein the second pair of electrodes is electrically connected together as the other of either the anode or the cathode.

2. A medical electrical lead of claim 1, wherein the first pair of electrodes is diagonally electrically connected.

3. A medical electrical lead of claim 1, wherein the second pair of electrodes is diagonally electrically connected.

4. A medical electrical lead of claim 1, wherein the first electrode is linearly connected to the second electrode.

5. A medical electrical lead of claim 1, wherein the third electrode is linearly connected to the fourth electrode.

6. The device according to claim 1 wherein the plurality of electrodes further comprises a third pair of electrodes comprising a fifth electrode and a sixth electrode diagonally spaced apart from each other and electrically connected.

7. The device according to claim 6 wherein the plurality of electrodes further comprises a fourth pair of electrodes comprising a seventh electrode and a eighth electrode diagonally spaced apart from each other and electrically connected.

8. The device according to claim 7, wherein the plurality of electrodes is located solely on a distal end of the lead forms a minimum of 16 pacing vectors.

9. The device according to claim 7, wherein the plurality of electrodes is located solely on a distal end of the lead forms a minimum of 12 or more pacing vectors.

10. The device according to claim 7, wherein the plurality of electrodes is located solely on a distal end of the lead forms a minimum of 8 or more pacing vectors.

11. The device according to claim 7, wherein the plurality of electrodes is located solely on a distal end of the lead forms a minimum of 4 or more pacing vectors.

12. A implantable medical device comprising:
    a housing;
    a connector block coupled to the housing;
    a medical electrical lead coupled to the connector block, the lead comprising an elongated lead body having a length between a proximal end and a distal end with a longitudinal axis extending between the proximal end and the distal end,
    a plurality of electrodes, located along the distal end of the lead body, the plurality of electrodes parsed into first and second pairs of electrodes in which the first pair of electrodes comprising a first electrode electrically connected to a second electrode by means of a first jumper conductor within the lead body while diagonally and circumferentially spaced apart, and the second pair of electrodes comprising a third electrode electrically connected to a fourth electrode by means of a second jumper conductor within the lead body while diagonally and circumferentially spaced apart;
    a first conductor extending from the connector block and directly connected to one of the first and second electrodes; and
    a second conductor extending from the connector block and directly connected to one of the third and fourth electrodes, wherein the first pair of electrodes is electrically connected together as one of either an anode or a cathode.

13. A implantable medical device comprising:
    a housing;
    a connector block coupled to the housing;
    a medical electrical lead coupled to the connector block, the lead comprising an elongated lead body having a length between a proximal end and a distal end with a longitudinal axis extending between the proximal end and the distal end,
    a plurality of electrodes, located along the distal end of the lead body, the plurality of electrodes parsed into first and second pairs of electrodes in which the first pair of electrodes comprising a first electrode electrically connected to a second electrode by means of a first jumper conductor within the lead body while diagonally and circumferentially spaced apart, and the second pair of electrodes comprising a third electrode electrically connected to a fourth electrode by means of a second jumper conductor within the lead body while diagonally and circumferentially spaced apart;
    a first conductor extending from the connector block and directly connected to one of the first and second electrodes; and
    a second conductor extending from the connector block and directly connected to one of the third and fourth electrodes, wherein the first pair of electrodes is electrically connected together as one of either an anode or a cathode, wherein the second pair of electrodes is dependent upon whether the first pair of electrodes is electrically connected together as one of either an anode or a cathode.

14. The device according to claim 13 wherein the plurality of electrodes further comprises a third pair of electrodes comprising a fifth electrode and a sixth electrode diagonally spaced apart from each other and electrically connected.

15. The device according to claim 14 wherein the plurality of electrodes further comprises a fourth pair of electrodes comprising a seventh electrode and a eighth electrode diagonally spaced apart from each other and electrically connected.

16. The device according to claim 15, wherein the plurality of electrodes is located solely on a distal end of the lead forms a minimum of 16 pacing vectors.

17. The device according to claim 15, wherein the plurality of electrodes is located solely on a distal end of the lead forms a minimum of 12 or more pacing vectors.

18. The device according to claim 15, wherein the plurality of electrodes is located solely on a distal end of the lead forms a minimum of 8 or more pacing vectors.

19. The device according to claim 15, wherein the plurality of electrodes is located solely on a distal end of the lead forms a minimum of 4 or more pacing vectors.

20. A implantable medical device comprising:
a housing;
a connector block coupled to the housing;
a medical electrical lead coupled to the connector block, the lead comprising an elongated lead body having a length between a proximal end and a distal end with a longitudinal axis extending between the proximal end and the distal end,
a plurality of electrodes, located along the distal end of the lead body, the plurality of electrodes parsed into first and second pairs of electrodes in which the first pair of electrodes comprising a first electrode electrically connected to a second electrode by means of a first jumper conductor within the lead body while diagonally and circumferentially spaced apart, and the second pair of electrodes comprising a third electrode electrically connected to a fourth electrode by means of a second jumper conductor within the lead body while diagonally and circumferentially spaced apart;
a first conductor extending from the connector block and directly connected to one of the first and second electrodes; and
a second conductor extending from the connector block and directly connected to one of the third and fourth electrodes,
wherein the second pair of electrodes are electrically connected together as an anode, wherein the first pair of electrodes are electrically connected together as a cathode.

21. The device according to claim 20 wherein the plurality of electrodes further comprises a third pair of electrodes comprising a fifth electrode and a sixth electrode diagonally spaced apart from each other and electrically connected.

22. The device according to claim 21 wherein the plurality of electrodes further comprises a fourth pair of electrodes comprising a seventh electrode and a eighth electrode diagonally spaced apart from each other and electrically connected.

23. The device according to claim 22, wherein the plurality of electrodes is located solely on a distal end of the lead forms a minimum of 16 pacing vectors.

24. The device according to claim 22, wherein the plurality of electrodes is located solely on a distal end of the lead forms a minimum of 12 or more pacing vectors.

25. The device according to claim 22, wherein the plurality of electrodes is located solely on a distal end of the lead forms a minimum of 8 or more pacing vectors.

26. The device according to claim 22, wherein the plurality of electrodes is located solely on a distal end of the lead forms a minimum of 4 or more pacing vectors.

* * * * *